(12) United States Patent
Old et al.

(10) Patent No.: US 9,591,935 B2
(45) Date of Patent: Mar. 14, 2017

(54) THERAPEUTIC SUBSTITUTED CYCLOPENTANES

(75) Inventors: David W. Old, Irvine, CA (US); Vinh X. Ngo, Huntington Beach, CA (US); Mark Holoboski, Irvine, CA (US); Mari Posner, Laguna Niguel, CA (US)

(73) Assignee: ALLERGEN, INC., Irvine, CA (US)

( * ) Notice: Subject to any disclaimer, the term of this patent is extended or adjusted under 35 U.S.C. 154(b) by 1741 days.

(21) Appl. No.: 12/667,197

(22) PCT Filed: Jun. 30, 2008

(86) PCT No.: PCT/US2008/068716
§ 371 (c)(1),
(2), (4) Date: May 19, 2014

(87) PCT Pub. No.: WO2009/006370
PCT Pub. Date: Jan. 8, 2009

(65) Prior Publication Data
US 2011/0062165 A1    Mar. 17, 2011

(51) Int. Cl.
| | | |
|---|---|---|
| A61K 31/38 | (2006.01) | |
| A61K 31/381 | (2006.01) | |
| A61K 31/41 | (2006.01) | |
| C07D 333/10 | (2006.01) | |
| A47G 19/06 | (2006.01) | |

(52) U.S. Cl.
CPC .................................. A47G 19/06 (2013.01)

(58) Field of Classification Search
CPC ...... A61K 31/381; A61K 31/38; A61K 31/41; C07D 333/10
USPC ..... 220/574, 574.1, 575; 206/557, 562, 563, 206/564, 1.7, 1.8; 294/144, 137, 164, 294/158, 172; D07/543; 248/309.1
See application file for complete search history.

(56) References Cited

U.S. PATENT DOCUMENTS

| | | | | |
|---|---|---|---|---|
| 2,307,882 | A * | 1/1943 | Freud et al. ................. | 220/23.4 |
| 3,980,700 | A | 9/1976 | Miyano | |
| 4,149,007 | A | 4/1979 | Buckler et al. | |
| 5,323,910 | A * | 6/1994 | van de Graaf, Jr. .......... | 206/557 |
| 5,390,798 | A * | 2/1995 | Yanuzzi ....................... | 206/562 |
| 5,536,725 | A | 7/1996 | Cullen et al. | |
| 5,593,062 | A * | 1/1997 | Martin ....................... | 220/574.1 |
| 5,727,678 | A * | 3/1998 | Chen ............................ | 206/217 |
| 5,950,856 | A * | 9/1999 | Cinque ........................ | 220/23.4 |
| 6,264,026 | B1 * | 7/2001 | Bradley ....................... | 206/217 |
| 6,531,485 | B2 | 3/2003 | Cameron | |
| 6,651,836 | B1 * | 11/2003 | Hofheins et al. ............. | 220/575 |
| 7,592,366 | B2 * | 9/2009 | Old ........................ | C07C 405/00 514/381 |
| 2003/0008895 | A1 | 1/2003 | Cameron et al. | |

FOREIGN PATENT DOCUMENTS

| | | |
|---|---|---|
| EP | 1108426 | 6/2001 |
| WO | 9858911 | 12/1998 |
| WO | 2006076370 | 7/2006 |
| WO | 2007149829 | 12/2007 |
| WO | 2008008660 | 1/2008 |
| WO | 2008008701 | 1/2008 |
| WO | 2008008718 | 1/2008 |

OTHER PUBLICATIONS

International Search Report and Written Opinion mailed Nov. 21, 2008 for PCT/US2008/068716 filed Jun. 30, 2008 in the name of Allergan, Inc.
U.S. Appl. No. 10/599,046, filed Dec. 13, 2007, Old.
(Continued)

Primary Examiner — Yong Chong
(74) Attorney, Agent, or Firm — Jonathan Bass

(57) ABSTRACT

Disclosed herein are compounds having the formula (I) wherein a dashed line represents the presence or absence of a bond; Y is an organic acid functional group, or an amide or ester thereof; or Y is hydroxymethyl or an ether thereof; or Y is a tetrazolyl functional group; A is —$(CH_2)_6$—, cis —$CH_2CH=CH-(CH_2)_3$—, or —$CH_2C\equiv C-(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—; $U^1$ and $U^2$ are independently selected from —H, =O, —OH, —F, —Cl, and —CN; and B is aryl or heteroaryl, for use as acular hypotensive agent.

(I)

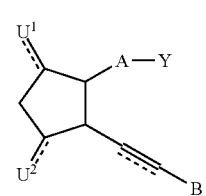

21 Claims, 4 Drawing Sheets

(56) References Cited

OTHER PUBLICATIONS

Figure 1:
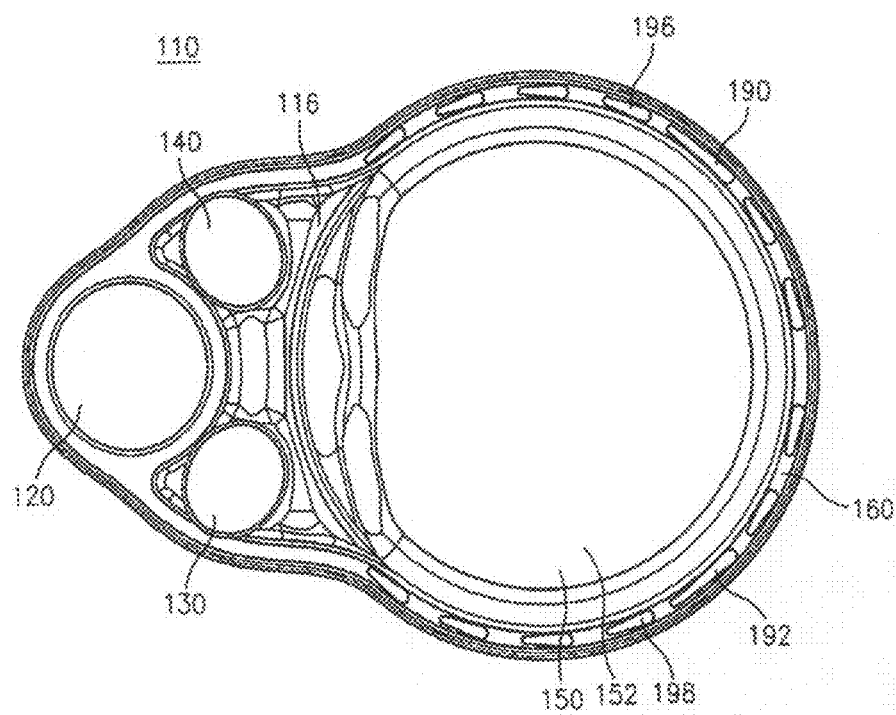
Figure 5:
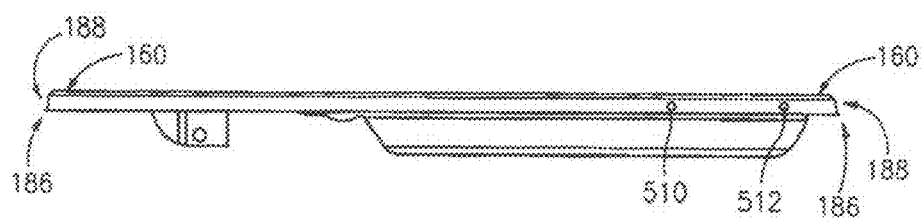
Figure 2:
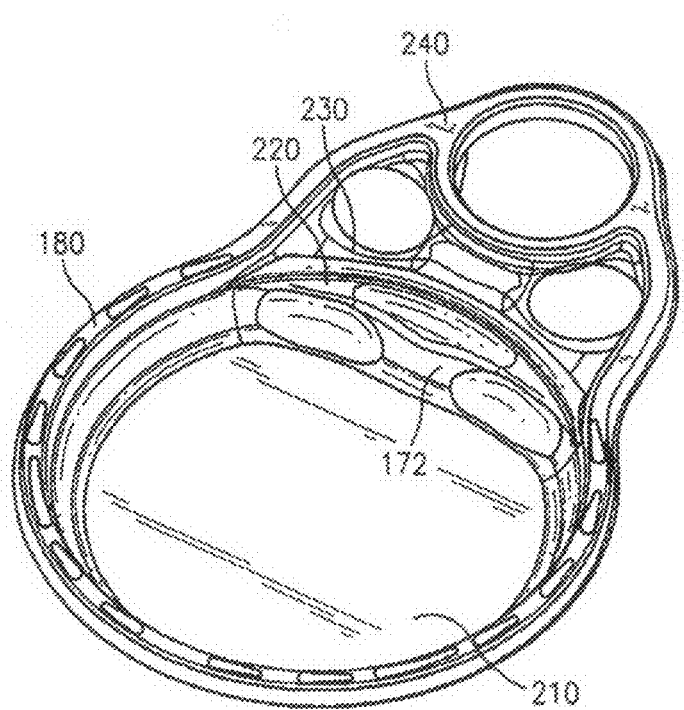
Figure 3:
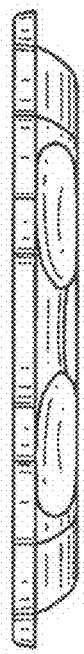
Figure 4:
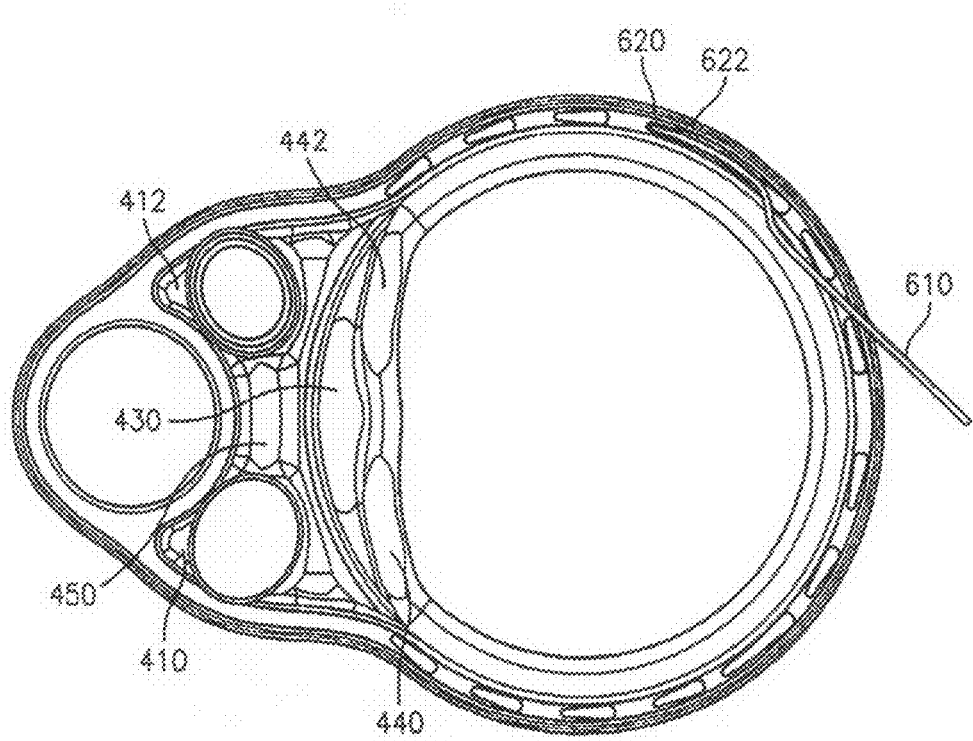
Figure 7:
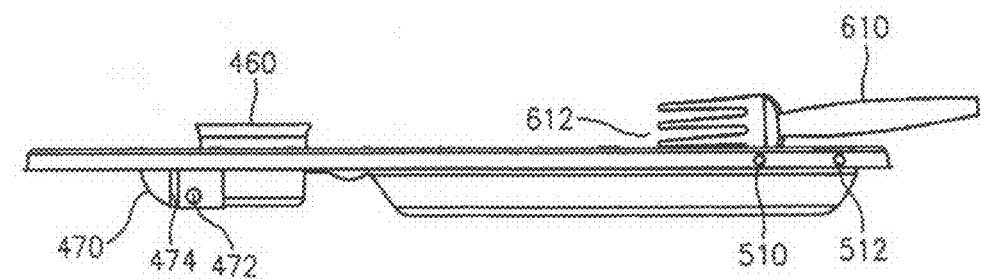
Figure 6:
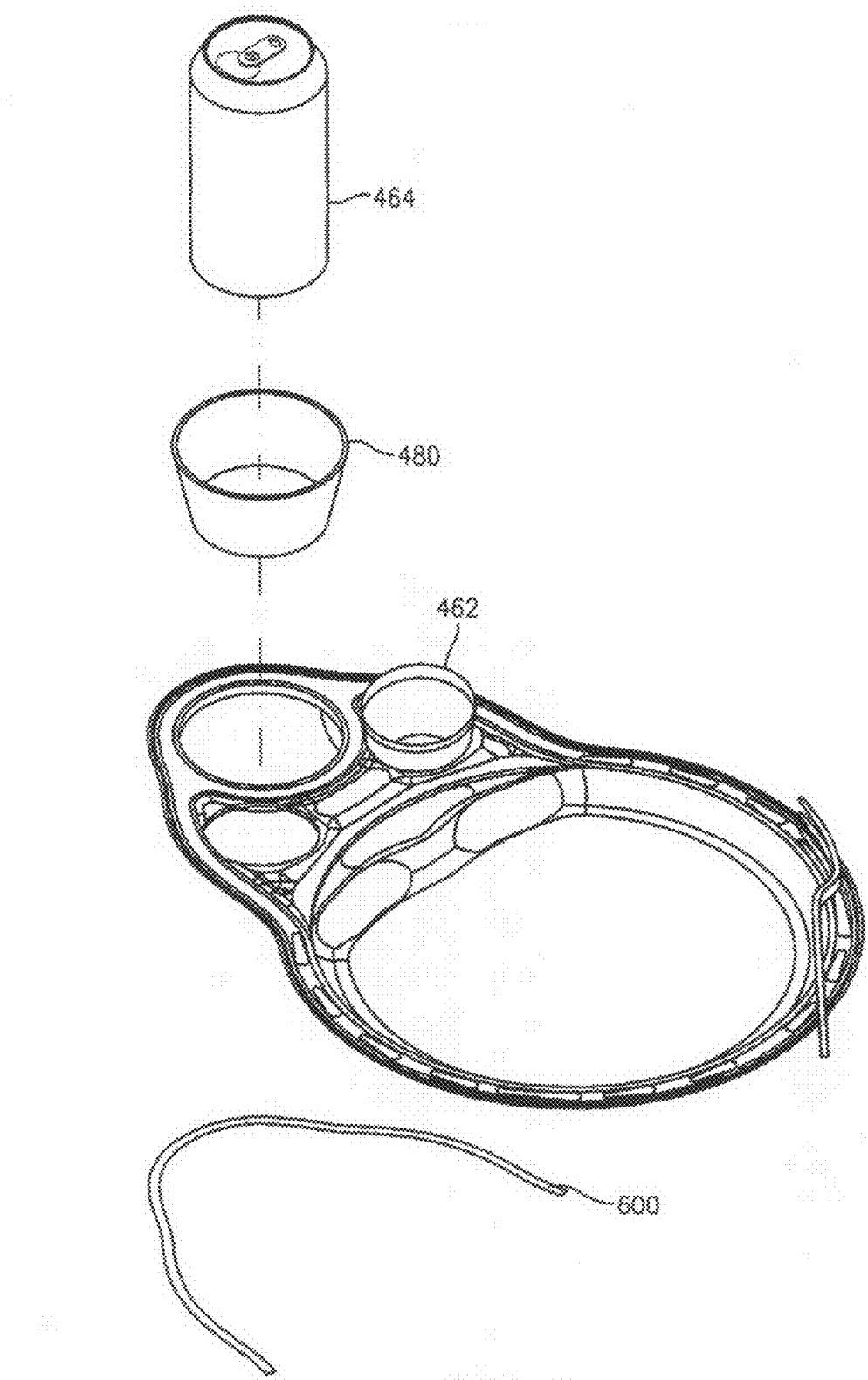

U.S. Appl. No. 60/805,285, filed Jun. 20, 2006, Old.
U.S. Appl. No. 60/806,947, filed Jul. 11, 2006, Old.
U.S. Appl. No. 11/553,143, filed Oct. 26, 2006, Old.
Prodrugs and Drug Delivery Systems, which is a chapter in Richard B. Silverman, Organic Chemistry of Drug Design and Drug Action, 2d Ed., Elsevier Academic Press: Amsterdam, 2004, pp. 496-557.
Furstner, et al Angew. Chem Int. Ed. 2002, 41, 609-612.
P. De Clercq "Prostaglandin Synthesis Involving Catalytic Hydrogenation of 2,3-Dialky1-4-Hydroxy-2-Cyylopentenones," State University of Ghent, Department of Organic Chemistry, Laboratory of Organic Synthesis, Krijgslaan, 271; 1976.
P. De Clercq "H-MNR Spectral Parameters of Some 1, 4-Dihydroxy-2, 3-Dialkylcyclopentanes: The configurational Dependant Magnitude of Some $^1$H-NMR Spectral Parameters," State University of Ghent, Department of Organic Chemistry, Laboratory of Organic Synthesis, Krijgslaan, 271; 1976.

* cited by examiner

THERAPEUTIC SUBSTITUTED CYCLOPENTANES

CROSS REFERENCE TO RELATED APPLICATIONS

This is a national stage application under 35 U.S.C. 371 of PCT patent application PCT/US08/68716, filed on Jun. 30, 2008, which claims the benefit of U.S. Provisional Patent Application 60/947,904, filed Jul. 3, 2007, each of which is hereby incorporated by reference in its entirety.

BACKGROUND

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

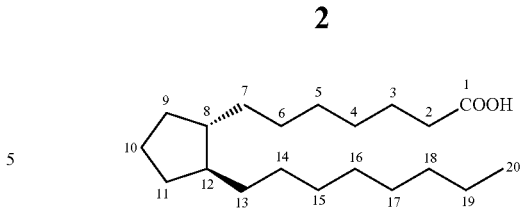

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ (PGF2β)].

DESCRIPTION OF THE INVENTION

Disclosed herein are compounds having a formula

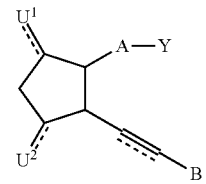

wherein a dashed line represents the presence or absence of a bond;
Y is an organic acid functional group, or an amide or ester thereof; or Y is hydroxymethyl or an ether thereof; or Y is a tetrazolyl functional group;
A is —($CH_2$)$_6$—, cis —$CH_2CH$=$CH$—($CH_2$)$_3$—, or —$CH_2C$≡$C$—($CH_2$)$_3$—, wherein 1 or 2 carbon atoms may be replaced by S or O; or A is —($CH_2$)$_m$—Ar—($CH_2$)$_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—;
$U^1$ and $U^2$ are independently selected from —H, =O, —OH, —F, —Cl, and —CN; and
B is aryl or heteroaryl.

These compounds are useful for the treatment of glaucoma and the reduction of intraocular pressure. The compound is incorporated into a dosage form or a medicament and administered to the mammal, such as a person, in need thereof. For example, a liquid composition may be administered as an eye drop or a solid or liquid dosage form may also be administered orally. Other types of dosage forms and medicaments are well known in the art, and may also be used here.

Another embodiment is a composition comprising a compound disclosed herein, wherein said composition is a liquid which is ophthalmically acceptable.

Another embodiment is a medicament comprising a compound disclosed herein, wherein said medicament is a liquid which is ophthalmically acceptable.

Another embodiment is a method comprising administering a compound disclosed herein to a mammal for the treatment of glaucoma or elevated intraocular pressure.

Another embodiment is a kit comprising a composition comprising compound disclosed herein, a container, and instructions for administration of said composition to a mammal for the treatment of glaucoma or elevated intraocular pressure.

Methods of formulating compounds such as those disclosed herein for ophthalmic and other pharmaceutical preparations are well known in the art. For example, U.S. patent application Ser. No. 10/599,046, filed on Sep. 18, 2006, incorporated by reference herein, describes typical formulation methods.

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Unless otherwise indicated, reference to a compound should be construed broadly to include pharmaceutically acceptable salts, prodrugs, tautomers, alternate solid forms, non-covalent complexes, and combinations thereof, of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate add or base, associated with one or more corresponding counterions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. While not intending to limit the scope of the invention, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Since the compounds have several potential stereocenters, several stereoisomers are possible. Therefore, compounds such as those having the structures shown below are contemplated.

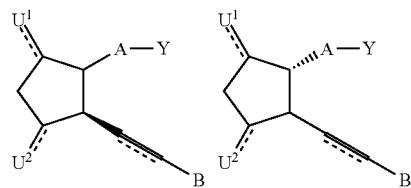

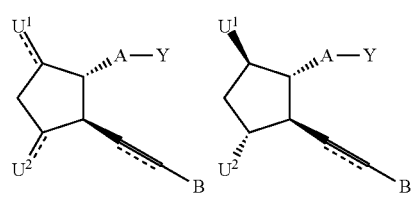

Double bonds can be cis or trans. Therefore, compounds according to the structural depictions below are contemplated.

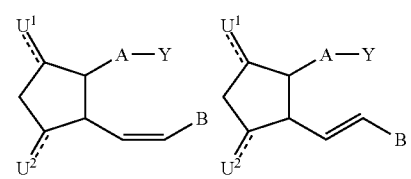

Since a dashed line represents the presence or absence of a bond, compounds according to the formula below are also contemplated.

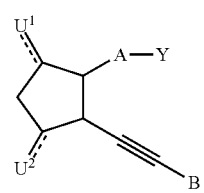

Y is an organic acid functional group, or an amide or ester thereof; or Y is hydroxymethyl or an ether thereof, or Y is a tetrazolyl functional group. For the purposes of this disclosure, Y is limited to from 0 to 14 carbon atoms and any necessary hydrogen atoms.

An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Esters and amides of organic functional groups are carbonyl groups directly attached to a nitrogen or oxygen atom. Thus, esters of amides of carboxylic acids, sulfonic acid, and phosphonic acid functional groups are depicted below.

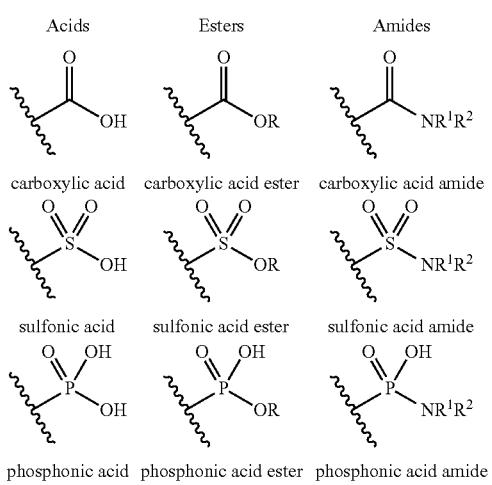

An amide may also have a —SO$_2$— moiety. For example the amide —CONHSO$_2$R$^3$, wherein R$^3$ is a hydrocarbyl of from 1 to 14 carbon atoms, is contemplated. R, R$^1$, R$^2$, and R$^3$ are hydrocarbyl subject to the constraint that Y may not have more than 14 carbon atoms.

An ether of hydroxymethyl is —CH$_2$OR.

An unsubstituted tetrazolyl functional group has two tautomeric forms, which can rapidly interconvert in aqueous or biological media, and are thus equivalent to one another. These tautomers are shown below.

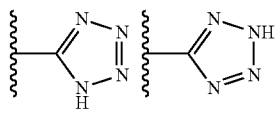

Additionally, if R$^2$ is C$_1$-C$_6$ alkyl, phenyl, or biphenyl, other isomeric forms of the tetrazolyl functional group such as the one shown below are also possible, unsubstituted and hydrocarbyl substituted tetrazolyl up to C$_{12}$ are considered to be within the scope of the term "tetrazolyl."

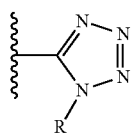

In one embodiment, Y is CO$_2$R$^4$, CONR$^6$R$^6$, CON(CH$_2$CH$_2$OH)$_2$, CONH(CH$_2$CH$_2$OH), CH$_2$OH, P(O)(OH)$_2$, CONHSO$_2$R$^4$, SO$_2$NR$^5$R$^6$,

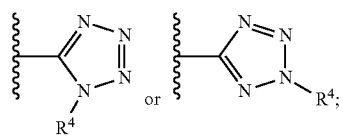

wherein R$^4$R$^5$ and R$^6$ are independently H, C$_1$-C$_6$ alkyl, unsubstituted phenyl, or unsubstituted biphenyl, provided that Y has no more than 14 carbon atoms.

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$— may be replaced by —CH═CH— or —C≡C—.

Thus, A may be —(CH$_2$)$_6$—, cis —CH$_2$CH═CH—(CH$_2$)$_3$—, or —CH$_2$C≡C—(CH$_2$)$_3$—.

Alternatively, A may be a group which is related to one of these three moieties in that any carbon is replaced with S or O. For example, A may be a moiety where S replaces one or two carbon atoms such as one of the following or the like.

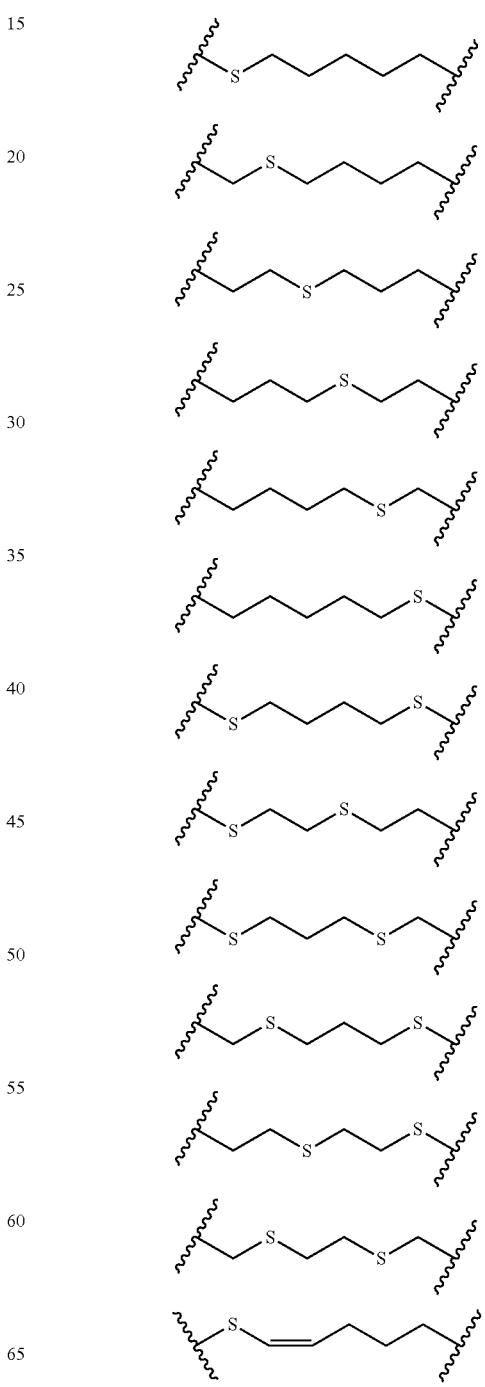

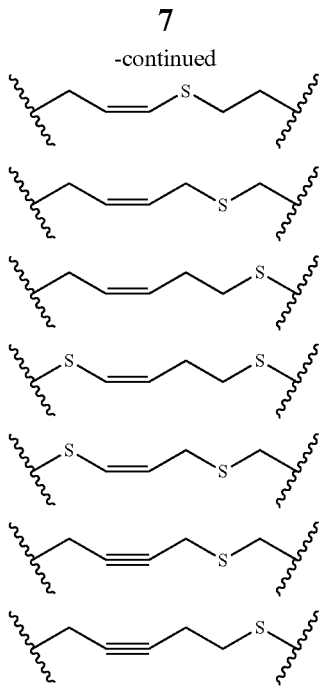

Alternatively, A may be a moiety where O replaces one or two carbon atoms such as one of the following or the like.

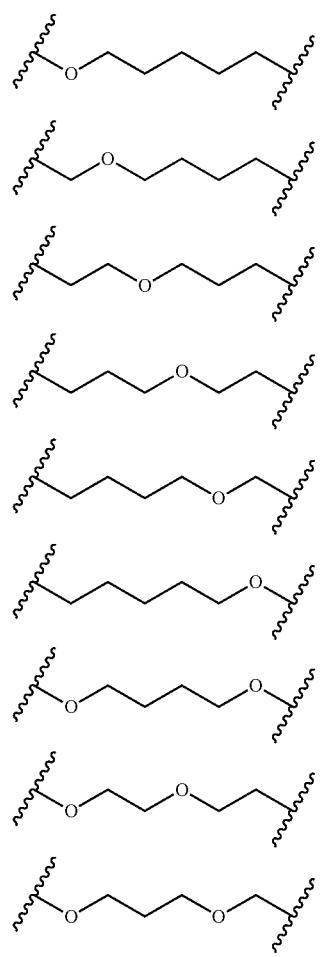

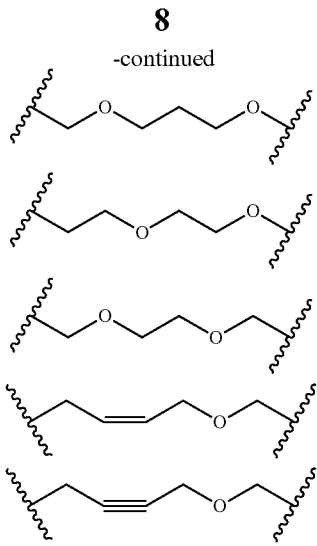

Alternatively, A may have an O replacing one carbon atom and an S replacing another carbon atom, such as one of the following or the like.

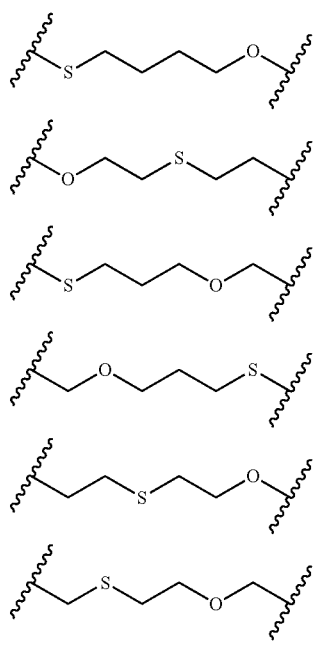

Alternatively, in certain embodiments A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—. In other words, in one embodiment A comprises:
1) a) 1, 2, 3, or 4 —$CH_2$— moieties, or
   b) 0, 1 or 2 —$CH_2$— moieties and —CH=CH— or —C≡C—; and
2) Ar;

e.g. —$CH_2$—Ar—, —$(CH_2)_2$—Ar—, —CH=CH—Ar—, —$CH_2$—Ar—$CH_2$—, —$CH_2$Ar—$(CH_2)_2$—, —$CH_2$Ar—CH=CH—, —$CH_2$Ar—C≡—, —$(CH_2)_2$Ar—$(CH_2)_2$—, and the like;

in another embodiment A comprises:
1) a) O; and 0, 1, 2, or 3 —CH$_2$— moieties; or
   b) O; and 0 or 1 —CH$_2$— moieties and —CH=CH— or —C≡C—; and
2) Ar;
e.g., —O—Ar—, —Ar—CH$_2$—O—, —O—Ar—(CH$_2$)$_2$—, —OAr—CH=CH—, —O—CH$_2$—Ar—(CH$_2$)$_2$, —O—CH$_2$Ar—CH=CH—, —O—CH$_2$Ar—C≡C—, and the like; or in another embodiment A comprises:
1) a) S; and 0, 1, 2, or 3 —CH$_2$— moieties; or
   b) S; and 0 or 1 —CH$_2$— moieties and —CH=CH— or and
2) Ar;
e.g., —S—Ar—, —Ar—CH$_2$—S—, —S—Ar—(CH$_2$)$_2$—, —SAr—CH=CH—, —S—CH$_2$—Ar—(CH$_2$)$_2$, —S—CH$_2$Ar—CH=CH—, —S—CH$_2$Ar—C≡C—, and the like.

In another embodiment, the sum of m and o is 2, 3, or 4 wherein one CH$_2$ may be replaced with S or O and 1 —CH$_2$—CH$_2$— may be replaced by —CH=CH— or —C≡C—.

In another embodiment, the sum of m and o is 3 wherein one CH$_2$ may be replaced with S or O and 1 —CH$_2$—CH$_2$— may be replaced by —CH=CH— or —C≡C—.

In another embodiment, the sum of m and o is 2 wherein one CH$_2$ may be replaced with S or O or 1 —CH$_2$—CH$_2$— may be replaced by —CH=CH— or —C≡C—.

In another embodiment, the sum of m and o is 4 wherein one CH$_2$ may be replaced with S or O and 1 —CH$_2$—CH$_2$— may be replaced by —CH=CH— or Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph).

In another embodiment A is —(CH$_2$)$_2$-Ph-. Substituents of Ar each have from 0 to 4 carbon atoms, from 0 to 3 oxygen atoms, from 0 to 2 sulfur atoms, from 0 to 2 nitrogen atoms, from 0 to 3 fluorine atoms, from 0 to 1 chlorine atoms, from 0 to 1 bromine atoms, from 0 to 1 iodine atoms, and from 0 to 10 hydrogen atoms.

In another embodiment A is —CH$_2$—Ar—OCH$_2$—. In another embodiment A is —CH$_2$-Ph-OCH$_2$—. In another embodiment, Ph is attached at the 1 and 3 positions, otherwise known as m-interphenylene, such as when A has the structure shown below.

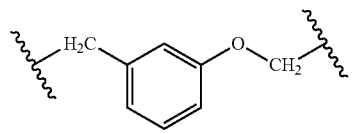 [SMILES: *COc1cccc(C*)c1]

In another embodiment A is —(CH$_2$)$_6$—, cis —CH$_2$CH=CH—(CH$_2$)$_r$—, or —CH$_2$C≡C—(CH$_2$)$_3$—, wherein 1 or 2 carbon atoms may be replaced with S or O; or A is —(CH$_2$)$_2$-Ph- wherein one —CH$_2$— may be replaced with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In one embodiment, Ar is thienyl.

In other embodiments, A has one of the following structures.

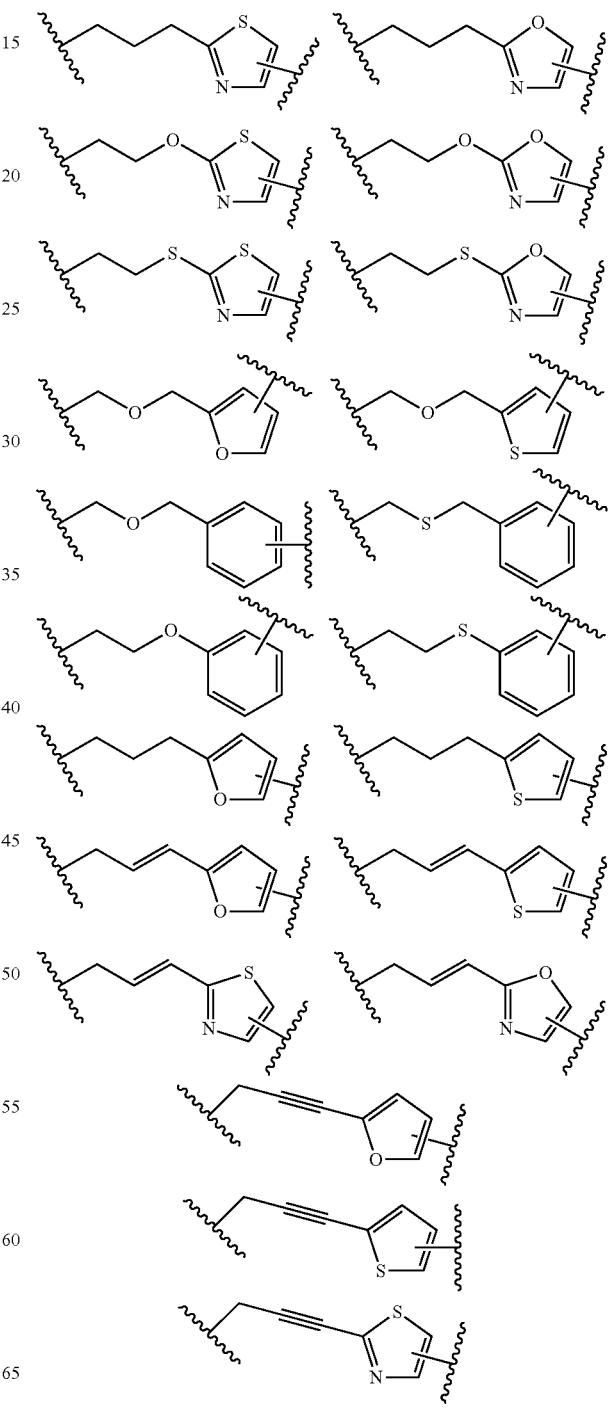

-continued

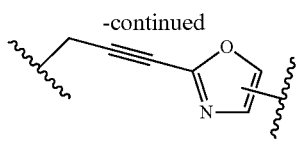

In another embodiment A is —CH$_2$OCH$_2$Ar—.
In another embodiment A is —CH$_2$SCH$_2$Ar—.
In another embodiment A is —(CH$_2$)$_3$Ar—.
In another embodiment A is —CH$_2$—O—(CH$_2$)$_4$—.
In another embodiment A is —CH$_2$S(CH$_2$)$_4$—.
In another embodiment A is —(CH$_2$) δ7.
In another embodiment A is cis —CH$_2$CH=CH—(CH$_2$)$_3$—.
In another embodiment A is —CH$_2$C≡C—(CH$_2$)$_3$—.
In another embodiment A is —S(CH$_2$)$_3$S(CH$_2$)$_2$—.
In another embodiment A is —(CH$_2$)$_4$OCH$_2$—.
In another embodiment A is cis —CH$_2$CH=CH—CH$_2$OCH$_2$—.
In another embodiment A is —CH$_2$CH≡CH—CH$_2$OCH$_2$—.
In another embodiment A is —(CH$_2$)$_2$S(CH$_2$)$_3$—.
In another embodiment A is —CH$_2$-Ph-OCH$_2$—, wherein Ph is interphenylene.
In another embodiment A is —CH$_2$-mPh-OCH$_2$—, wherein mPh is m-interphenylene.
In another embodiment A is —CH$_2$—O—(CH$_2$)$_4$—.
In another embodiment A is —CH$_2$—O—CH$_2$—Ar—, wherein Ar is 2,5-interthienylene.
In another embodiment A is —CH$_2$—O—CH$_2$—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-(methoxymethyl)phenyl.
In another embodiment A is 3-(3-propylphenyl).
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.

U$^1$ and U$^2$ are independently selected from —H, =O, —OH, —F, —Cl, and —CN. Thus, the compounds depicted in the structural formulas below are contemplated.

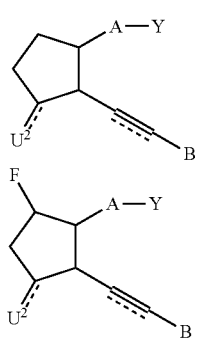
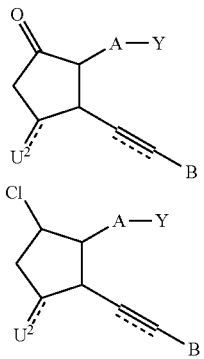
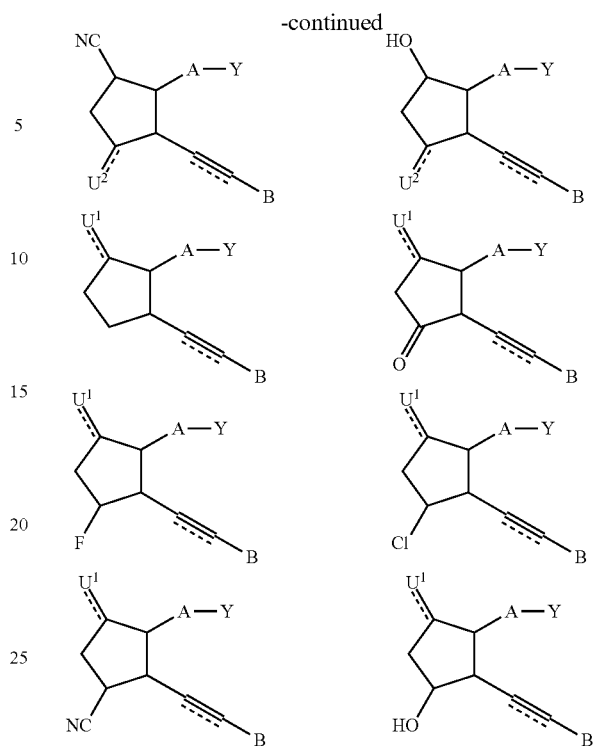

In one embodiment, U$^1$ is Cl and U$^2$ is OH.

B is substituted aryl or heteroaryl.

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

The substituents of B each have from 0 to 6 carbon atoms, from 0 to 3 oxygen atoms, from 0 to 2 sulfur atoms, from 0 to 2 nitrogen atoms, from 0 to 3 fluorine atoms, from 0 to 1 chlorine atoms, from 0 to 1 bromine atoms, from 0 to 1 iodine atoms, and from 0 to 14 hydrogen atoms.

The substituents on B may be the same or different. For example, B might have 2 chloro substituents, or B might have a chloro and a hydroxymethyl substituent.

The substituents of Ar and B are independent, but the types of substituents contemplated are similar. Thus, subject to the constraints described herein (i.e. limits on the number of atoms for a substituent), examples of substituents for Ar and B include, but are not limited to:

Hydrocarbyl, meaning a moiety consisting of carbon and hydrogen only, including, but not limited to:
  a. alkyl, meaning hydrocarbyl having no double or triple bonds, including, but not limited to:
    linear alkyl, e.g. methyl, ethyl, n-propyl, n-butyl, n-pentyl, n-hexyl, etc.,
    branched alkyl, e.g. iso-propyl, 1-butyl and other branched butyl isomers, branched pentyl isomers, etc.,
    cycloalkyl, e.g. cyclopropyl, cyclobutyl, cyclopentyl, cyclohexyl, etc.,
    combinations of linear, branched, and/or cycloalkyl;
  b. alkenyl, e.g. hydrocarbyl having 1 or more double bonds, including linear, branched, or cycloalkenyl c. alkynyl, e.g. hydrocarbyl having 1 or more triple bonds, including linear, branched, or cycloalkenyl;

d. combinations of alkyl, alkenyl, and/or akynyl alkyl-CN, such as —$CH_2$—CN, —$(CH_2)_2$—CN; —$(CH_2)_3$—CN, and the like;

hydroxyalkyl, i.e. alkyl-OH, such as hydroxymethyl, hydroxyethyl, and the like;

ether substituents, including —O-alkyl, alkyl-O-alkyl, and the like;

thioether substituents, including —S-alkyl, alkyl-5-alkyl, and the like;

amine substituents, including —$NH_2$, —NH-alkyl, —N-$alkyl^1 alkyl^2$ (i.e., $alkyl^2$ and $alkyl^2$ are the same or different, and both are attached to N), alkyl-$NH_2$, alkyl-NH-alkyl, alkyl-N-$alkyl^1 alkyl^2$, and the like;

aminoalkyl, meaning alkyl-amine, such as aminomethyl (—$CH_2$-amine), aminoethyl, and the like;

ester substituents, including —$CO_2$-alkyl, —$CO_2$-phenyl, etc.;

other carbonyl substituents, including aldehydes; ketones, such as acyl

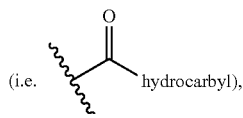

(i.e. hydrocarbyl), and the like; in particular, acetyl, propionyl, and benzoyl substituents are contemplated;

phenyl or substituted phenyl;

fluorocarbons or hydrofluorocarbons such as —$CF_3$, $CH_2 CF_3$, etc.; and

—CN;

combinations of the above are also possible, subject to the constraints defined;

Alternatively, a substituent may be —F, —Cl, —Br, or —I.

In particular, alkyl having from 1 to 6 carbon atoms is contemplated as a substituent.

Alternatively, alkyl having from 1 to 4 carbon atoms is contemplated;

Substituents must be sufficiently stable to be stored in a bottle at room temperature under a normal atmosphere for at least 12 hours, or stable enough to be useful for any purpose disclosed herein.

If a substituent is a salt, for example of a carboxylic acid or an amine, the counter-ion of said salt, i.e. the ion that is not covalently bonded to the remainder of the molecule is not counted for the purposes of the number of heavy atoms in a substituent. Thus, for example, the salt —$CO_2^- Na^+$ is a stable substituent consisting of 1 carbon atom and 2 oxygen atoms, i.e. sodium is not counted. In another example, the salt —$NH(Me)_2^+ Cl^-$ is a stable substituent consisting of 1 nitrogen atom, three carbon atoms, and 7 hydrogen atoms, i.e. chlorine is not counted.

In one embodiment, B is substituted or unsubstituted phenyl or pyridinyl.

In one embodiment the substituents of B are Cl, F, $CH_3$, $CH_2 OH$, or OH.

Another embodiment is a compound having a formula

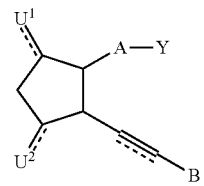

wherein a dashed line represents the presence or absence of a bond;

Y is an organic acid functional group, or an amide or ester thereof; or Y is hydroxymethyl or an ether thereof; or Y is a tetrazolyl functional group;

A is —$(CH_2)_6$—, cis —$CH_2 CH$=CH—$(CH_2)_3$—, or —$CH_2 C$≡C—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—;

$U^1$ and $U^2$ are independently selected from —H, =O, —OH, —F, —Cl, and —CN; and B is aryl or heteroaryl, provided that if $U^1$ is =O, $U^2$ is not —OH or —H.

Another embodiment is a compound having a formula

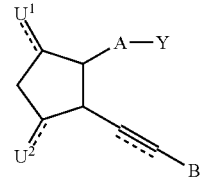

wherein a dashed line represents the presence or absence of a bond;

Y is an organic acid functional group, or an amide or ester thereof; or Y is hydroxymethyl or an ether thereof; or Y is a tetrazolyl functional group;

A is —$(CH_2)_6$—, cis —$CH_2 CH$=CH—$(CH_2)_3$—, or —$CH_2 C$≡C—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—;

$U^1$ is —H, —OH, —F, —Cl, or —CN;

$U^2$ is —H, =O, —OH, —F, —Cl, or —CN; and

B is aryl or heteroaryl.

Another embodiment is a compound having a formula

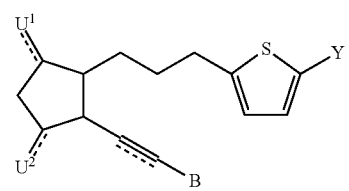

wherein a dashed line represents the presence or absence of a bond;

Y is an organic acid functional group, or an amide or ester thereof; or Y is hydroxymethyl or an ether thereof, or Y is a tetrazolyl functional group;

$U^1$ and $U^2$ are independently selected from —H, =O, —OH, —F, —Cl, and —CN; and B is aryl or heteroaryl.

In another embodiment $U^1$ is =O.
In another embodiment $U^1$ is —H.
In another embodiment $U^1$ is —OH.
In another embodiment $U^1$ is —F.
In another embodiment $U^1$ is —Cl.
In another embodiment $U^1$ is —CN.
In another embodiment $U^2$ is =O.
In another embodiment $U^2$ is —H.
In another embodiment $U^2$ is —OH.
In another embodiment $U^2$ is —F.
In another embodiment $U^2$ is —Cl.
In another embodiment $U^2$ is —CN.

Another embodiment is a compound having a formula

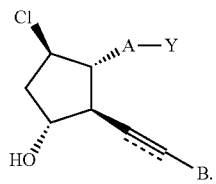

In another embodiment, B is substituted with substituents selected from F, Cl, $C_{1-3}$ alkyl, and hydroxyalkyl having from 1 to 3 carbon atoms.

In another embodiment, B is selected from

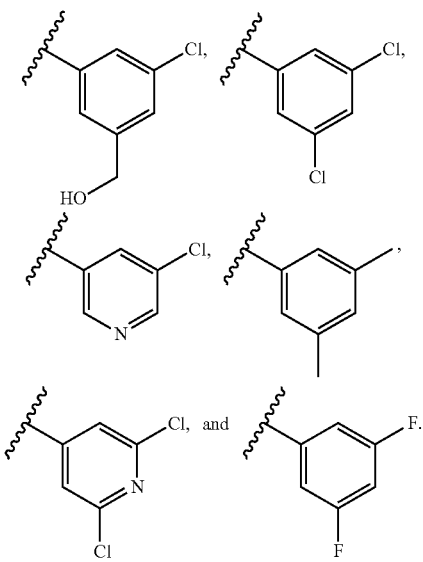

Another embodiment is a compound selected from:

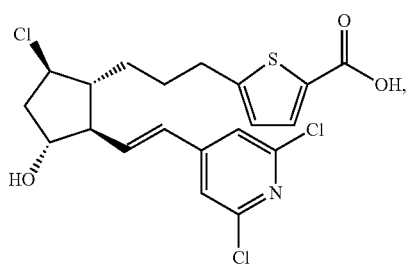

-continued

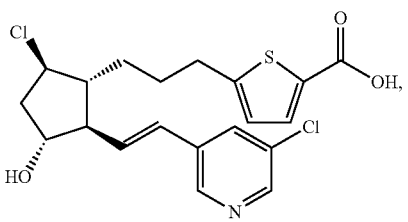

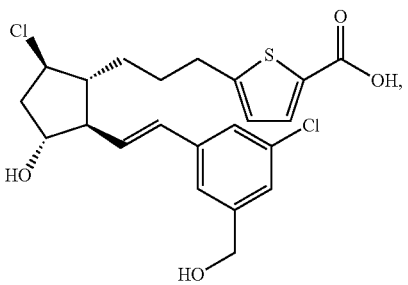

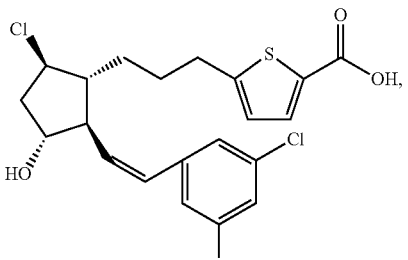

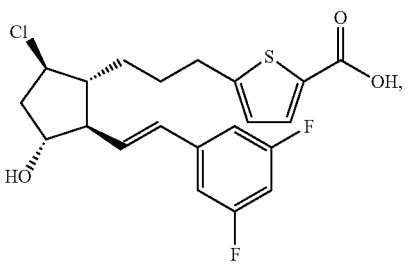

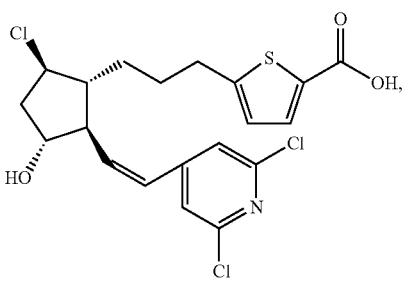

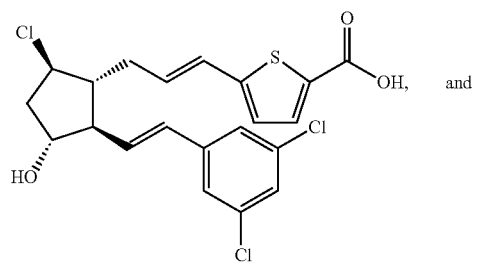

and

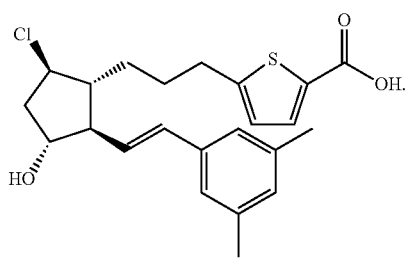
Some hypothetical examples of useful compounds are shown below.
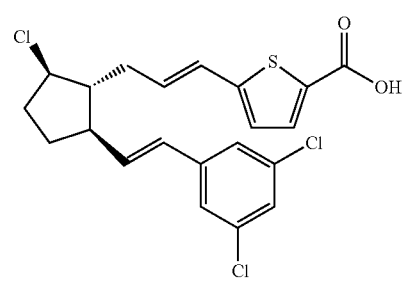
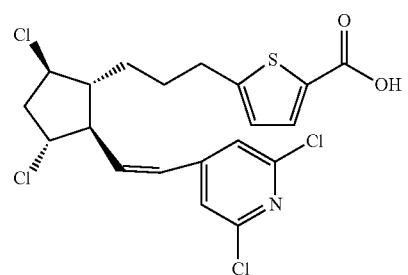
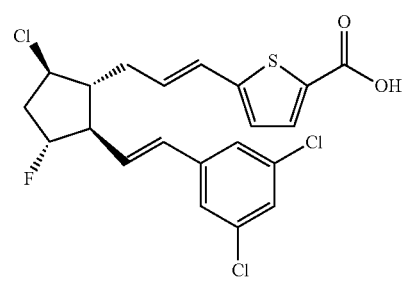
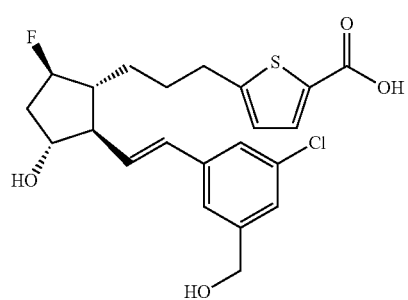
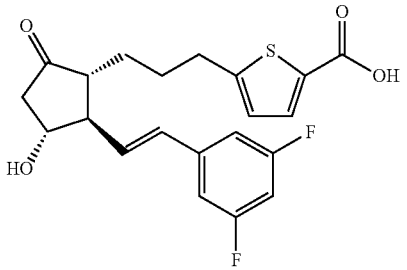
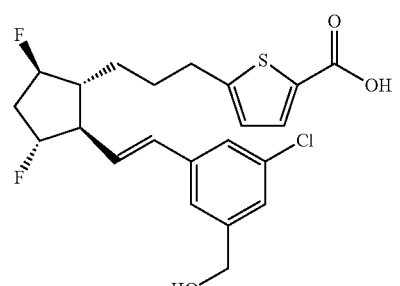
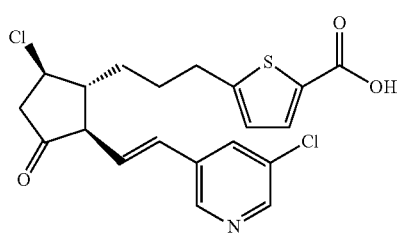
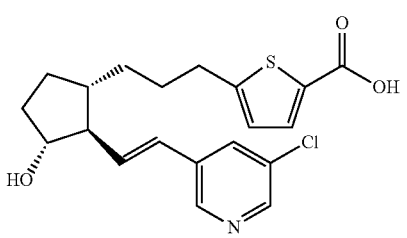
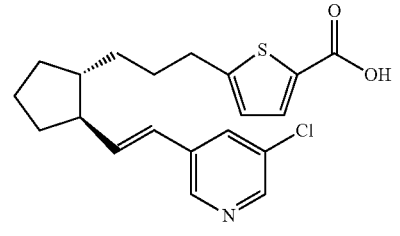
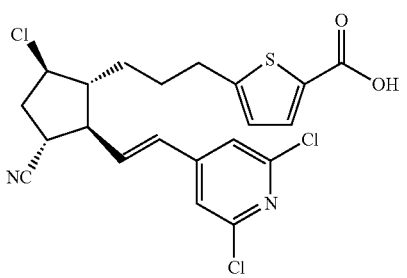

19
-continued
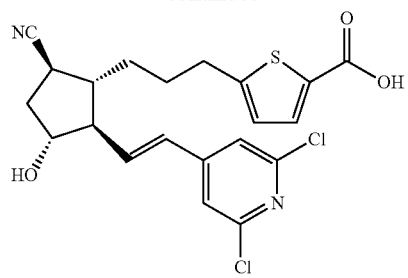
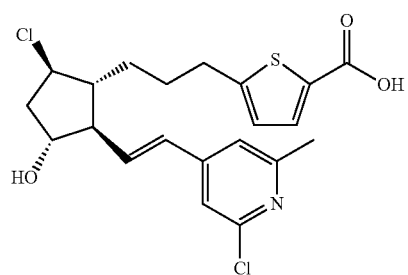
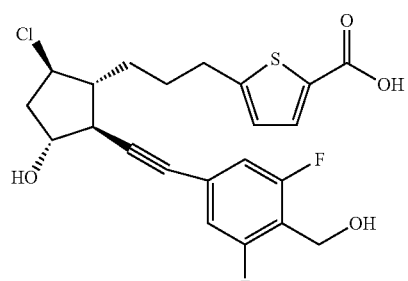
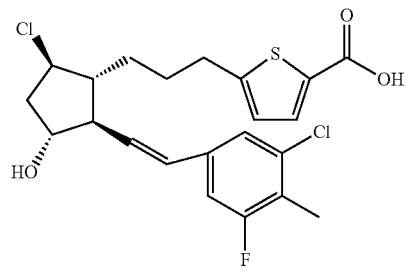
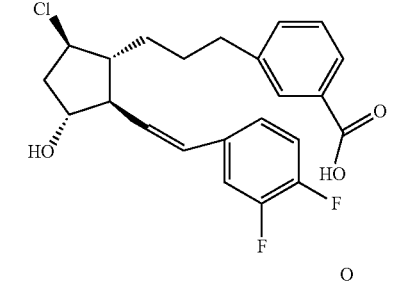
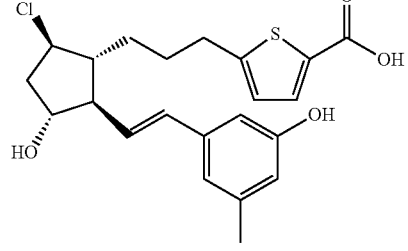
20
-continued
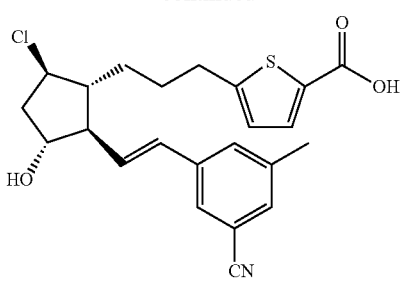
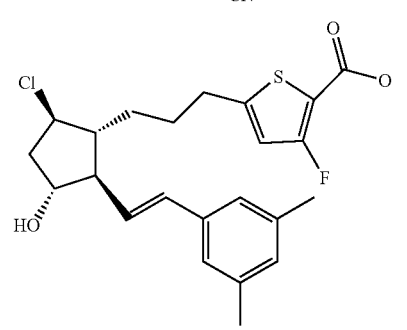
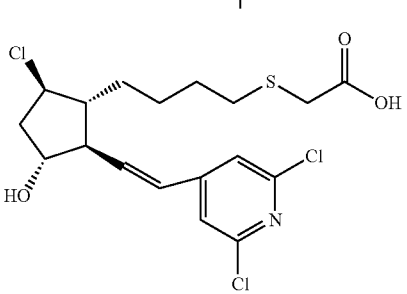
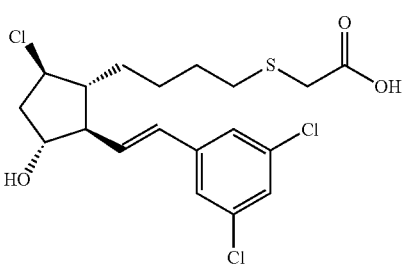
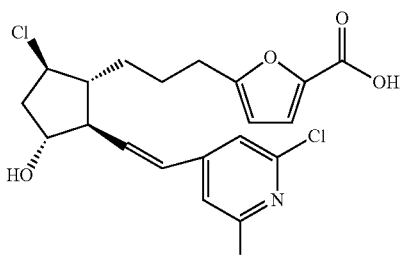
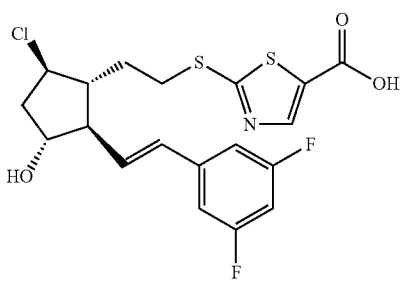

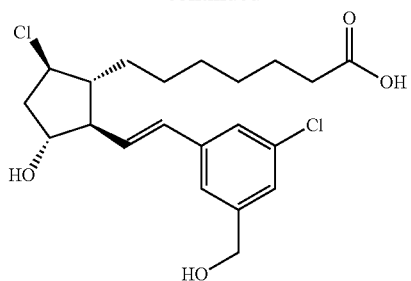
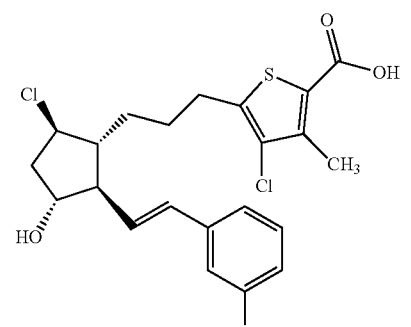
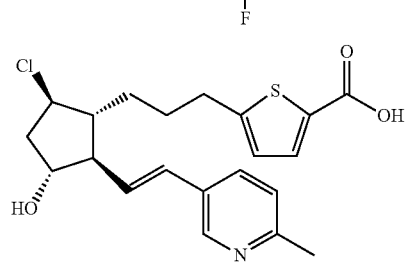
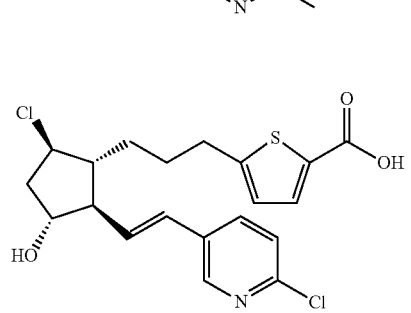
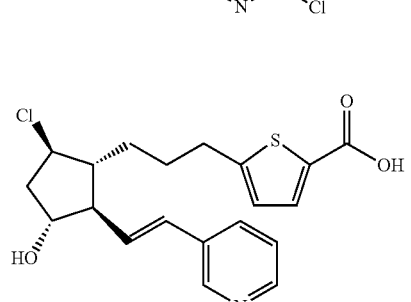
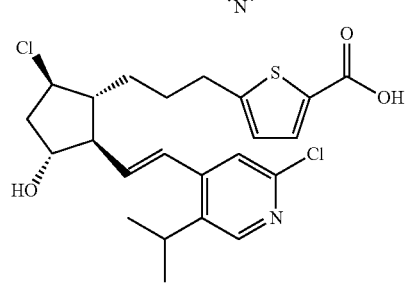
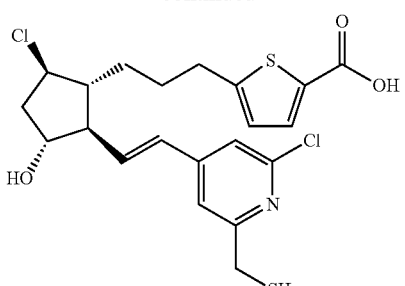
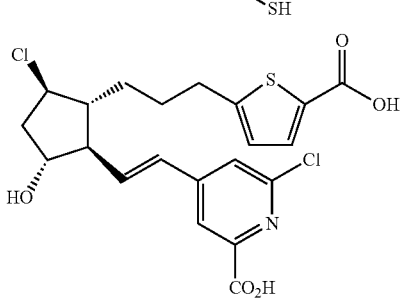
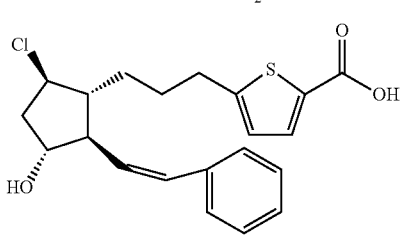
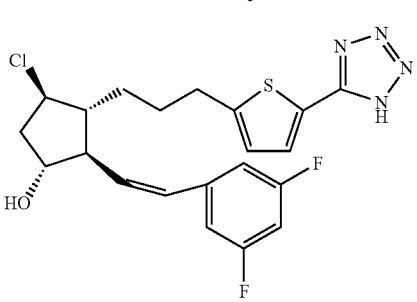
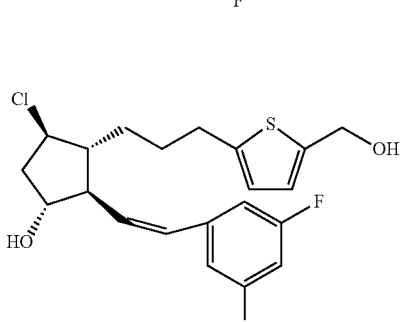
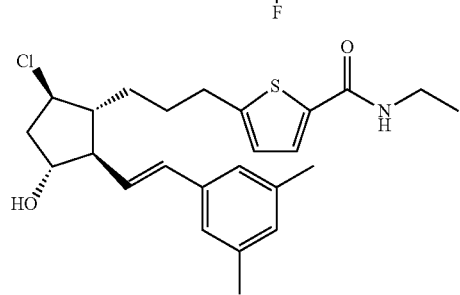

-continued

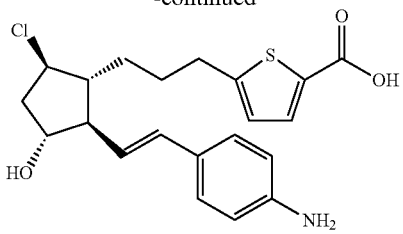

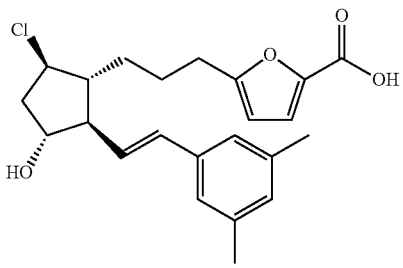

Synthetic Methods

Example 1

5-(3-((1R,2R,3R,5R)-5-chloro-2-(3,5-dichlorostyryl)-3-hydroxycyclopentyl)prop-1-enyl)thiophene-2-carboxylic acid (8)

Step 1. Mesylation of 1 to Give 2

Triethylamine (4.2 mL, 30.0 mmol) and methanesulfonyl chloride (1.9 mL, 24.1 mmol) were added sequentially to a solution of 1 (see U.S. Prov. Pat. App. No. 60/805,285, 10.1 g, 19.9 mmol) in $CH_2Cl_2$ (100 mL) at 0° C. The reaction mixture was allowed to warm to room temperature and stirred at room temperature for 3 h. Saturated aqueous $NaHCO_3$ (4.00 mL) was added and the mixture was extracted with $CH_2Cl_2$ (3×400 mL). The combined organic extracts were washed with water (200 mL) and brine (200 mL), then dried ($MgSO_4$), filtered and concentrated in vacuo to afford 11.5 g (~98%) of the desired mesylate 2, which was used without further purification.

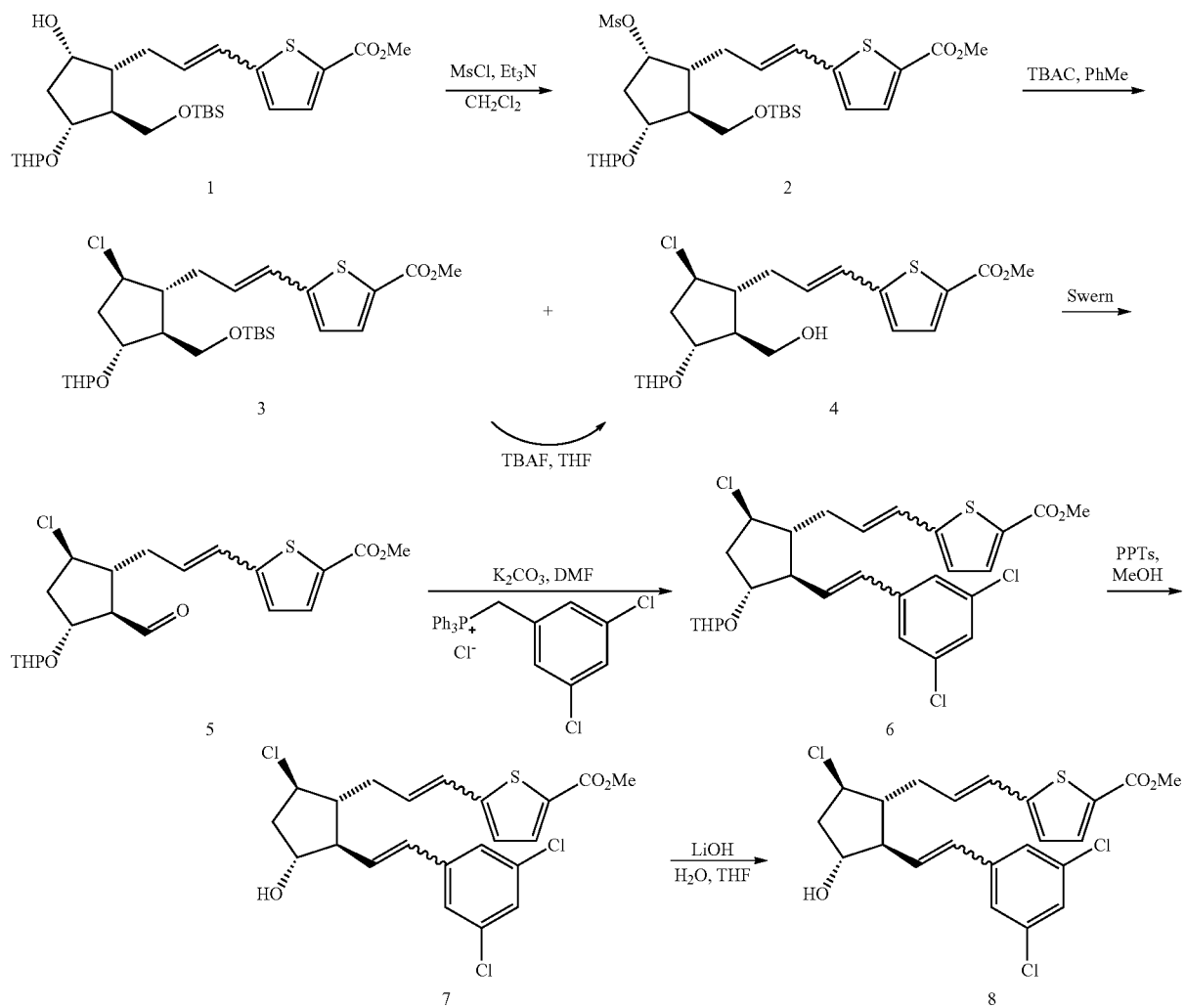

Step 2. Conversion of Mesylate 2 to Chloride 3 and Alcohol 4

Tetrabutylammonium chloride (26.5 g, 95.4 mmol) was added to a solution of 2 (11.5 g, 19.5 mmol) in toluene (200 mL). The reaction mixture was heated at 45° C. for 18 h. TLC analysis indicated that much of the starting mesylate remained, so the reaction mixture was heated at 50° C. for 4 h. The cooled mixture was partitioned between water (200 mL) and EtOAc (500 mL). The phases were separated and the organic phase was washed with water (4×200 mL). The combined aqueous phase was back-extracted with EtOAc (350 mL). The combined organic phase was dried (MgSO$_4$), filtered and concentrated in vacuo. Purification of the crude residue by chromatography on 120 g silica gel (hexane→EtOAc, gradient) afforded 2.6 g (25%) of chloride 3 and 1.8 g (22%) of alcohol 4.

Step 3. Desilylation of 3 to Give Alcohol 4

Tetrabutylammonium fluoride (14.7 mL of a 1.0 M THF solution, 14.7 mmol) was added to a solution of 3 (2.6 g, 4.91 mmol) in THF (15 mL) at room temperature. After 18 h at room temperature, the reaction mixture was partitioned between EtOAc (50 mL) and water (50 mL). The phases were separated and the organic phase was washed with water (3×50 mL). The combined aqueous phase was back-extracted with EtOAc (100 mL). The combined organic phase was dried (MgSO$_4$), filtered and concentrated in vacuo. Purification of the crude residue by chromatography on 40 g silica gel (hexane→EtOAc, gradient) afforded 1.23 g (60%) of alcohol 4.

Step 4. Oxidation of 4 to Give 5

DMSO (1.5 mL, 21.1 mmol) was added to a solution of oxalyl chloride (4.4 mL of a 2.0 M solution in CH$_2$Cl$_2$, 8.8 mmol) in CH$_2$Cl$_2$ (5 mL) at −78° C. After 30 min, a solution of alcohol 4 (3.03 g, 7.30 mmol) in CH$_2$Cl$_2$ (42 mL) was added slowly via syringe. After 15 min at −78° C., triethylamine (9.0 mL, 64.6 mmol) was added. After 1.5 h at −78° C., the reaction was allowed to warm to room temperature. After 2 h at room temperature the reaction mixture was partitioned between saturated aqueous NaHCO$_3$ (100 mL) and CH$_2$Cl$_2$ (300 mL). The phases were separated and the aqueous phase was extracted with CH$_2$Cl$_2$ (2×200 mL). The combined extracts were dried (MgSO$_4$), filtered and concentrated in vacuo to afford ~3.0 g of crude aldehyde 5, which was used without further purification.

Step 5. Wittig Reaction of 5 to Afford Diene 6

Potassium carbonate (99.99%, 5.0 g, 36.2 mmol) and 3,5-dichlorophenylmethyltriphenylphosphonium chloride (see Cullen, et al., U.S. Pat. No. 5,536,725, 6.7 g, 14.6 mmol) were added to a solution of aldehyde 5 (crude from previous step, ~3.0 g, ~7.3 mmol) in DMF (73 mL) at room temperature. After 18 h the reaction mixture was partitioned between water (100 mL) and EtOAc (300 mL). The phases were separated and the organic phase was washed with water (9×100 mL). The combined aqueous phase was back-extracted with EtOAc (300 mL). The combined organic phase was dried (MgSO$_4$), filtered and concentrated in vacuo. Purification of the crude residue by chromatography on silica gel (CH$_2$Cl$_2$) afforded 3.0 g (74%) of diene 6.

Step 6. Deprotection of 6 to Give 7

Pyridinium p-toluenesulfonate (PPTs, 550 mg, 2.19 mmol) was added to a solution of 6 (3.0 g, 5.40 mmol) in methanol (100 mL) at room temperature under nitrogen. The solution was heated at 40° C. for 18 h, then cooled and concentrated in vacuo. Purification of the crude residue by chromatography on 12 g silica gel (CH$_2$Cl$_2$) afforded 1.7 g (67%) of alcohol 7 as a mixture of olefin isomers.

Step 7. Saponification of 7 to Give 8

Lithium hydroxide (0.89 mL of a 1.0 M aqueous solution, 0.89 mmol) was added to a solution of ester 7 (84 mg, 0.18 mmol) in THF (0.89 mL). The solution was heated at 40° C. for 18 h, then cooled to room temperature. The mixture was partitioned between 1.0 M aqueous HCl (5 mL) and EtOAc (5 mL). The phases were separated and the organic phase was washed with water (5 mL), dried (MgSO$_4$), filtered and concentrated in vacuo. Purification of the crude residue by chromatography on 4 g silica gel (CH$_2$Cl$_2$→10% MeOH/CH$_2$Cl$_2$, gradient) afforded 48 mg (59%) of the title compound as a mixture of olefin isomers.

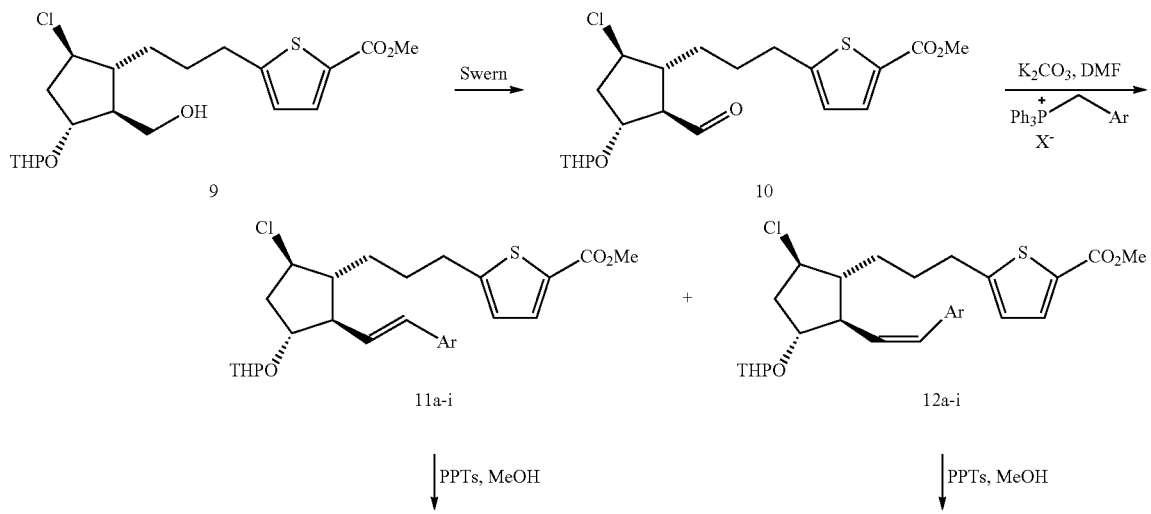

Scheme 2

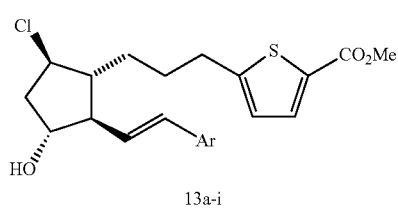

13a-i

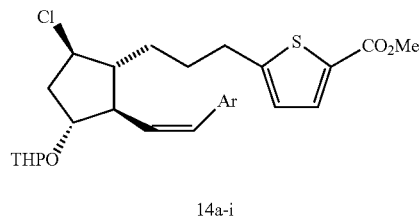

14a-i

↓ LiOH, H₂O, THF

↓ LiOH, H₂O, THF

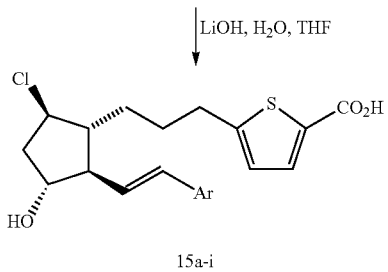

15a-i

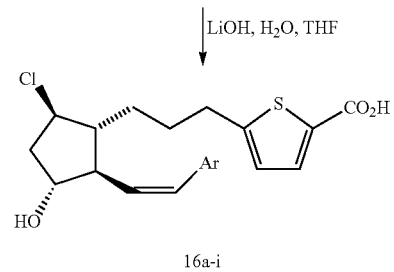

16a-i

Example 2

5-(3-((1R,2R,3R,5R)-5-chloro-2-(3-chloro-5-(hydroxymethyl)styryl)-3-hydroxycyclopentyl)propyl)-thiophene-2-carboxylic acid (15a)

Step 1. Oxidation of 9 to Give 10

DMSO (32 μL 0.45 mmol) was added to a solution of oxalyl chloride (0.1 mL of a 2.0 M solution in CH₂Cl₂, 0.2 mmol) in CH₂Cl₂ (0.3 mL) at −78° C. After 30 min, a solution of alcohol 9 (see U.S. Prov. Pat App. No. 60/805, 285, 70 mg, 0.17 mmol) in CH₂Cl₂ (0.54 mL) was added via syringe. After 15 min at −78° C., triethylamine (187 μL 1.34 mmol) was added and the reaction was allowed to warm to room temperature. After 5 h at room temperature the reaction mixture was partitioned between saturated aqueous NaHCO₃ (10 mL) and CH₂Cl₂ (20 mL). The phases were separated and the aqueous phase was extracted with CH₂Cl₂ (2×10 mL). The combined organic phase was dried (MgSO₄), filtered and concentrated in vacuo to afford 69 mg of crude aldehyde 10, which was used without further purification.

Step 2. Wittig Reaction of 10 to Afford 11a

Potassium carbonate (99.99%, 232 mg, 1.68 mmol) was added to a solution of aldehyde 10 (crude from previous step, 69 mg, ~0.17 mmol) and 3-chloro-5-(hydroxymethyl)benzyltriphenylphosphonium chloride (Preparation 1, 150 mg, 0.33 mmol) in DMF (1.6 mL) at room temperature. After 18 h the reaction mixture was partitioned between water (30 mL) and EtOAc (50 mL). The phases were separated and the organic phase was washed with water (3×30 mL) and brine (30 mL) then dried (MgSO₄), filtered and concentrated in vacuo. Purification of the crude residue by chromatography on 4 g silica gel (hexane→EtOAc, gradient) afforded 35 mg (38%) of alkene 11a (contaminated with ~5% cis-olefin 12a).

Step 3. Deprotection of 11a to Give 13a

PPTs (16 mg, 0.006 mmol) was added to a solution of 11a (35 mg, 0.06 mmol) in methanol (0.6 mL) at room temperature under nitrogen. The solution was heated at 40° C. for 18 h, then cooled and concentrated in vacuo. Purification of the crude residue by chromatography on 4 g silica gel (hexane→EtOAc, gradient) afforded 28 mg (94%) of alcohol 13a (contaminated with ~5% cis-olefin 14a).

Step 4. Saponification of 13a to Give 15a

Lithium hydroxide (0.04 mL of a 1.0 M aqueous solution, 0.04 mmol) was added to a solution of ester 13a (5 mg, 0.011 mmol) in THF (0.05 mL). After 18 h, the mixture was partitioned between 1.0 M aqueous HCl (1 mL) and CH₂Cl₂ (5 mL). The phases were separated and the aqueous phase was extracted with CH₂Cl₂ (5 mL). The combined organic phase was dried (MgSO₄), filtered and concentrated in vacuo. Purification of the crude residue by chromatography on 4 g silica gel (CH₂Cl₂→20% MeOH/CH₂Cl₂, gradient) afforded 3 mg (62%) of the title compound (contaminated with ~5% cis-olefin 16a).

Example 3

5-(3-((1R,2R,3R,5R)-5-chloro-2-((E)-2-(5-chloro-pyridin-3-yl)vinyl)-3-hydroxycyclopentyl)propyl)-thiophene-2-carboxylic acid (15b)

Step 1. Wittig Reaction of 10 to Afford 11b

In accordance with the procedure of example 2, step 2, aldehyde 10 (190 mg, 0.46 mmol) and ((5-chloro-3-pyridinyl)methyl)triphenylphosphonium chloride (Preparation 2, 100 mg, 0.24 mmol) were converted into 104 mg (84%) of alkene 11b (contaminated with ~5% cis-olefin 12b).

Step 2. Deprotection of 11b to Give 13b

In accordance with the procedure of example 2, step 3, THP-ether 11b (104 mg, 0.20 mmol) was converted into 40 mg (46%) of alkene 13b (contaminated with ~5% cis-olefin 14b).

Step 3. Saponification of 13b to Give 15b

In accordance with the procedure of example 2, step 4, ester 13b (10 mg, 0.023 mmol) was converted into 3 mg (31%) of the title compound (contaminated with ~5% cis-olefin 16b).

Example 4

5-(3-((1R,2R,3R,5R)-5-chloro-2-((E)-2-(2,6-dichloropyridin-4-yl)vinyl)-3-hydroxycyclopentyl)propyl)-thiophene-2-carboxylic acid (15c)

Step 1. Wittig Reaction of 10 to Afford 11c and 12c

In accordance with the procedure of example 2, step 2, aldehyde 10 (290 mg, 0.70 mmol) and ((2,6-dichloro-4-pyridinyl)methyl)triphenylphosphonium chloride (Preparation 3, 325 mg, 0.71 mmol) were converted into 200 mg (51%) of alkene 11c and 8 mg (2%) of alkene 12c and 108 mg (28%) of a mixture of 11c and 12c.

Step 2. Deprotection of 11c/12c to Give 13c/14c

In accordance with the procedure of example 2, step 3, a mixture of 11c and 12c (229 mg, 0.41 mmol) was converted into 169 mg (87%) of alkene 13c and 22 mg (11%) of alkene 14c.

Step 3. Saponification of 13c to Give 15c

Lithium hydroxide (0.23 mL of a 1.0 M aqueous solution, 0.23 mmol) was added to a solution of ester 13c (14 mg, 0.029 mmol) in THF (0.46 mL). After 66 h, the mixture was concentrated under a stream of nitrogen, diluted with water (2 mL) and acidified with 1.0 M aqueous HCl (1 mL). The mixture was extracted with EtOAc (3×10 mL). The combined organic phase was washed with brine (5 mL), dried ($Na_2SO_4$), filtered and concentrated in vacuo. Purification of the crude residue by chromatography on 4 g silica gel ($CH_2Cl_2 \rightarrow 15\%$ $MeOH/CH_2Cl_2$, gradient) afforded 4.5 mg (33%) of the title compound.

Example 5

5-(3-((1R,2R,3R,5R)-5-chloro-2-((Z)-2-(2,6-dichloropyridin-4-yl)vinyl)-3-hydroxycyclopentyl)propyl)-thiophene-2-carboxylic acid (16c)

In accordance with the procedure of example 4, step 3, ester 14c (22 mg, 0.046 mmol) was converted into 3.5 mg (16%) of the title compound, employing a reaction time of 18 h.

Example 6

5-(3-((1R,2R,3R,5R)-5-chloro-2-((E)-3,5-difluorostyryl)-3-hydroxycyclopentyl)propyl)thiophene-2-carboxylic add (15d)

Step 1. Wittig Reaction of 10 to Afford 11d and 12d

In accordance with the procedure of example 2, step 2, aldehyde 10 (250 mg, 0.60 mmol) and ((3,5-difluorophenyl)methyl)triphenylphosphonium chloride (Preparation 4, 422 mg, 0.90 mmol) were converted into 200 mg (63%) of an inseparable mixture of alkenes 11d and alkene 12d.

Step 2. Deprotection of 11d/12d to Give 13d/14d

In accordance with the procedure of example 2, step 3, a mixture of 11d and 12d (200 mg, 0.38 mmol) was converted into 120 mg (71%) of alkene 13d and 20 mg (12%) of alkene 14d.

Step 3. Saponification of 13d to Give 15d

In accordance with the procedure of example 2, step 4, ester 13d (20 mg, 0.045 mmol) was converted into 5 mg (26%) of the title compound.

Example 7

5-(3-((1R,2R,3R,5R)-5-chloro-2-((Z)-3,5-difluorostyryl)-3-hydroxycyclopentyl)propyl)thiophene-2-carboxylic acid (16d)

In accordance with the procedure of example 2, step 4, ester 14d (20 mg, 0.045 mmol) was converted into 3.9 mg (20%) of the title compound.

Example 8

5-(3-((1R,2R,3R,5R)-5-chloro-2-(3,5-dimethylstyryl)-3-hydroxycyclopentyl)propyl)thiophene-2-carboxylic acid (15e)

Step 1. Wittig Reaction of 10 to Afford 11e

In accordance with the procedure of example 2, step 2, aldehyde 10 (250 mg, 0.60 mmol) and ((3,5-dimethylphenyl)methyl)triphenylphosphonium chloride (Preparation 5, 375 mg, 0.90 mmol) were converted into 250 mg (80%) of alkene 11e (contaminated with ~10% cis-olefin 12e).

Step 2. Deprotection of 11e to Give 13e

In accordance with the procedure of example 2, step 3, 11e (250 mg, 0.48 mmol) was converted into 195 mg (93%) of alkene 13e (contaminated with ~10% cis-olefin 14e).

Step 3. Saponification of 13e to Give 15e

In accordance with the procedure of example 2, step 4, ester 13e (10 mg, 0.023 mmol) was converted into 3 mg (31%) of the title compound (contaminated with ~10% cis-olefin 16e).

Preparation 1

(3-Chloro-5-(hydroxymethyl)benzyl)triphenylphosphonium chloride

Step 1. Methyl 3-chloro-5-(hydroxymethyl)benzoate

Sodium borohydride (1.1 g, 29.1 mmol) was added to a solution of dimethyl 5-chloroisophthalate (2.0 g, 8.7 mmol) in methanol (10 mL) and $CH_2Cl_2$ (10 mL). The reaction mixture was heated at 35° C. for 18 h then cooled to room temperature. The mixture was treated with water (50 mL) and extracted with $CH_2Cl_2$ (3×200 mL). The combined organic phase was dried ($MgSO_4$), filtered and concentrated in vacuo to afford crude methyl 3-chloro-5-(hydroxymethyl) benzoate that was used without further purification.

Step 2. Methyl 3-((tert-butyldimethylsilyloxy) methyl)-5-chlorobenzoate

Imidazole (3.6 g, 52.9 mmol) and TBSCl (4.0 g, 26.5 mmol) were added to a solution of crude methyl 3-chloro-5-(hydroxymethyl)benzoate (~8.7 mmol) in DMF (100 mL). After 18 h the reaction mixture was partitioned between water (100 mL) and EtOAc (200 mL). The phases were separated and the organic phase was washed with water (4×100 mL) and brine (100 mL) then dried ($MgSO_4$), filtered and concentrated in vacuo to afford crude methyl 3-((tert-butyldimethylsilyloxy)methyl)-5-chlorobenzoate that was used without further purification.

Step 3. (3-((tert-Butyldimethylsilyloxy)methyl)-5-chlorophenyl)methanol

Sodium borohydride (1.1 g, 29.1 mmol) was added to a solution of crude methyl 3-((tert-butyldimethylsilyloxy) methyl)-5-chlorobenzoate (~8.7 mmol) in methanol (10 mL) and $CH_2Cl_2$ (10 mL). After 18 h at room temperature, the reaction mixture was concentrated in vacuo. Citric add (5% aqueous, 50 mL) was added and the mixture was extracted with $CH_2Cl_2$ (50 mL). The organic phase was washed with water (50 mL) and brine (50 mL), then dried ($MgSO_4$), filtered and concentrated in vacuo. Purification of the crude residue by chromatography on 12 g silica gel (hexanes→EtOAc, gradient) afforded 920 mg (37% over three steps) of (3-((tert-butyldimethylsilyloxy)methyl)-5-chlorophenyl) methanol.

Step 4. tert-Butyl-(3-chloro-5-(chloromethyl)benzyloxy)dimethylsilane

Triethylamine (0.78 mL, 5.6 mmol) and methanesulfonyl chloride (0.31 mL, 4.0 mmol) were added to a solution of (3-((tert-butyldimethylsilyloxy)methyl)-5-chlorophenyl) methanol (460 mg, 1.6 mmol) in $CH_2Cl_2$ (1.6 mL) at 0° C. and the mixture was allowed to warm to room temperature. After 18 h at room temperature, the reaction was treated with saturated aqueous $NaHCO_3$ (50 mL) and extracted with $CH_2Cl_2$ (3×20 mL). The combined organic phase was dried ($MgSO_4$), filtered and concentrated in vacuo. Purification of the crude residue by chromatography on 4 g silica gel (hexanes→EtOAc, gradient) afforded 100 mg (20%) of tert-butyl-(3-chloro-5-(chloromethyl)benzyloxy)dimethylsilane.

Step 5. 3-Chloro-5-(hydroxymethyl)benzyl)triphenylphosphonium chloride

Triphenylphosphine (128 mg, 0.49 mmol) was added to a solution of tert-butyl-(3-chloro-5-(chloromethyl)benzyloxy) dimethylsilane (100 mg, 0.33 mmol) in toluene (0.6 mL) and the reaction mixture was heated to 100° C. After 18 h the reaction was cooled to room temperature and the solid material was isolated by filtration. After washing with excess toluene and drying in vacuo, 150 mg (quant.) of the title compound was isolated as a colorless solid.

Preparation 2

((5-Chloro-3-pyridinyl)methyl)triphenylphosphonium chloride

Step 1. Methyl 5-chloronicotinate

Concentrated $H_2SO_4$ (105 μL, 1.26 mmol) was added to a solution of 5-chloronicotinic acid (1.0 g, 6.35 mmol) in methanol (12.7 mL) and the mixture was heated at reflux. After 18 h, the mixture was cooled to room temperature then partitioned between water (200 mL) and $CH_2Cl_2$ (200 mL) and carefully neutralized with solid $K_2CO_3$. The phases were separated and the aqueous phase was extracted with $CH_2Cl_2$ (200 mL). The combined organic phase was dried ($MgSO_4$), filtered and concentrated in vacuo to afford 1.2 g of crude methyl 5-chloronicotinate that was used without further purification.

Step 2. (5-Chloropyridin-3-yl)methanol

Sodium borohydride (790 mg, 20.9 mmol) was added to a solution of crude methyl 5-chloronicotinate (~6.35 mmol) in methanol (10 mL) and $CH_2Cl_2$ (10 mL). After 18 h at room temperature, the reaction mixture was concentrated in vacuo. Water (50 mL) was added and the mixture was extracted with $CH_2Cl_2$ (3×50 mL). The organic phase was dried ($MgSO_4$), filtered and concentrated in vacuo. Purification of the crude residue by chromatography on 40 g silica gel (hexanes→EtOAc, gradient) afforded 510 mg (56% over two steps) of (5-chloropyridin-3-yl)methanol.

Step 3. 3-Chloro-5-(chloromethyl)pyridine

Triethylamine (1.75 mL, 12.6 mmol) and methanesulfonyl chloride (0.69 mL, 8.9 mmol) were added to a solution of (5-chloropyridin-3-yl)methanol (510 mg, 3.6 mmol) in $CH_2Cl_2$ (3.5 mL) at 0° C. and the reaction was allowed to warm to room temperature. After 18 h at room temperature, the reaction was partitioned between water (50 mL) and $CH_2Cl_2$ (50 mL). The phases were separated and the organic phase was extracted with $CH_2Cl_2$ (20 mL). The combined organic phase was dried ($MgSO_4$), filtered and concentrated in vacuo. Purification of the crude residue by chromatography on 12 g silica gel (hexanes→EtOAc, gradient) afforded 300 mg (52%) of 3-chloro-5-(chloromethyl)pyridine.

Step 4. ((5-Chloro-3-pyridinyl)methyl)triphenylphosphonium chloride

In accordance with the procedure of preparation 1, step 5,3-chloro-5-(chloromethyl)pyridine (300 mg, 1.85 mmol) was converted into 100 mg (13%) of the title compound.

Preparation 3

((2,6-Dichloro-4-pyridinyl)methyl)triphenylphosphonium chloride

In accordance with the procedure of preparation 1, step 5,2,6-dichloro-4-(chloromethyl)pyridine (1.0 g, 5.1 mmol) was converted into 2.0 g (86%) of the title compound.

Preparation 4

((3,5-Difluorophenyl)methyl)triphenylphosphonium chloride

In accordance with the procedure of preparation 1, step 5, 1-(bromomethyl)-3,5-difluorobenzene (1.0 g, 4.8 mmol) was converted into 1.8 g (79%) of the title compound.

Preparation 5

((3,5-Dimethylphenyl)methyl)triphenylphosphonium chloride

Step 1. 1-(Chloromethyl)-3,5-dimethylbenzene

Triethylamine (72 mL, 51.7 mmol) and methanesulfonyl chloride (2.86 mL, 36.8 mmol) were added to a solution of (3,5-dimethylphenyl)methanol (2.0 g, 14.7 mmol) in $CH_2Cl_2$ (25 mL) at 0° C. and the mixture was allowed to warm to room temperature. After 18 h at room temperature, the reaction was treated with saturated aqueous $NaHCO_3$ (100 mL) and extracted with $CH_2Cl_2$ (3×100 mL). The combined organic phase was washed with brine (100 mL), dried ($MgSO_4$), filtered and concentrated in vacuo. Purification of the crude residue by chromatography on 40 g silica gel (hexanes→EtOAc, gradient) afforded 1.5 g (66%) of 1-(chloromethyl)-3,5-dimethylbenzene.

Step 2. ((3,5-dimethylphenyl)methyl)triphenylphosphonium chloride

In accordance with the procedure of preparation 1, step 5, 1-(chloromethyl)-3,5-dimethylbenzene (1.5 g, 9.7 mmol) was converted into 600 mg (15%) of the title compound.

This procedure may be readily adapted by a person of ordinary to obtain a variety of other compounds. For example, U.S. Provisional Patent Application Ser. No. 60/806,947, filed on Jul. 11, 2006, incorporated by reference herein, describes methods that may be adapted to prepare compounds with a variety of different moieties for A, $U^1$ and $U^2$.

Preparation 6

((3-(But-3-enyl)phenyl)methyl)triphenylphosphonium chloride

Step 1. (3-(but-3-enyl)phenyl)methanol $LiAlH_4$ (10.0 mL of a 1.0 M solution in THF, 10.0 mmol) was added to a 0° C. solution of ethyl 3-(but-3-enyl) benzoate (commercially available from Reike Metals, Inc., 1.94 g, 9.5 mmol) in THF (35 mL). After 2 h at 0° C. the reaction was carefully quenched with water (50 mL). 10% aqueous NaOH (50 mL) was added and the mixture was extracted with $CH_2Cl_2$ (3×50 mL). The extracts were washed with brine (50 mL) then dried ($MgSO_4$), filtered and concentrated in vacuo. Purification of the crude residue by chromatography on 40 g silica gel (hexanes→EtOAc, gradient) afforded 1.7 g (somewhat impure, quant crude) of (3-(but-3-enyl)phenyl)methanol.

Step 2. 1-(but-3-enyl)-3-(chloromethyl)benzene

Triethylamine (2.0 mL, 14.4 mmol) and methanesulfonyl chloride (0.90 mL, 11.6 mmol) were added to a solution of (3-(but-3-enyl)phenyl)methanol (~9.5 mmol) in $CH_2Cl_2$ (20 mL) at 0° C. and the mixture was allowed to warm to rt. After 18 h at rt, the reaction was treated with saturated aqueous $NaHCO_3$ (50 mL) and extracted with $CH_2Cl_2$ (3×50 mL). The combined organic phase was washed with brine (50 mL), dried ($MgSO_4$), filtered and concentrated in vacuo. Purification of the crude residue by chromatography on 40 g silica gel (hexanes→EtOAc, gradient) afforded 1.6 g (93%) of 1-(but-3-enyl)-3-(chloromethyl)benzene.

Step 3. ((3-(but-3-enyl)phenyl)methyl)triphenylphosphonium chloride

In accordance with the procedure of preparation 1, step 5, 1-(but-3-enyl)-3-(chloromethyl)benzene (1.6 g, 8.9 mmol) was converted into 2.2 g (56%) of the title compound.

Example 9

5-(3-((1R,2R,3R,5R)-2-(3-(but-3-enyl)styryl)-5-chloro-3-hydroxycyclopentyl)propyl)thiophene-2-carboxylic acid (15f)

Step 1. Wittig Reaction of 10 to Afford 11f

In accordance with the procedure of example 2, step 2, aldehyde 10 (250 mg, 0.60 mmol) and ((3-(but-3-enyl) phenyl)methyl)triphenylphosphonium chloride (Preparation 6, 450 mg, 1.02 mmol) were converted into 220 mg (67%) of alkene 11f (contaminated with ~5% cis-olefin 12f).

Step 2. Deprotection of 11f to Give 13f

In accordance with the procedure of example 2, step 3, THP-ether 11f (220 mg, 0.41 mmol) was converted into 164 mg (88%) of alkene 13f (contaminated with ~5% cis-olefin 14f).

Step 3. Saponification of 13f to Give 15f

In accordance with the procedure of example 2, step 4, ester 13f (30 mg, 0.065 mmol) was converted into 8.3 mg (29%) of the title compound (15f, contaminated with ~5% cis-olefin 16f).

Preparation 7

(E)-(3-chloro-5-(prop-1-enyl)benzyl)triphenylphosphonium bromide

Step 1. methyl 3-chloro-5-((tetrahydro-2H-pyran-2-yloxy)methyl)benzoate

Dihydropyran (1.5 mL, 16.4 mmol) and PPTs (290 mg, 1.15 mmol) were added to a solution of methyl 3-chloro-5-(hydroxymethyl)benzoate (see preparation 1, step 1, 1.30 g, 6.5 mmol) in $CH_2Cl_2$ (20 mL). The mixture was heated at 40° C. After 18 h, the reaction mixture was cooled, concentrated in vacuo, and purified by chromatography on 40 g silica gel (hexanes→EtOAc, gradient) to afford 1.80 g, (98%) of methyl 3-chloro-5-((tetrahydro-2H-pyran-2-yloxy) methyl)benzoate.

Step 2. (3-chloro-5-((tetrahydro-2H-pyran-2-yloxy) methyl)phenyl)methanol

Sodium borohydride (834 mg, 22.0 mmol) was added to a solution of methyl 3-chloro-5-((tetrahydro-2H-pyran-2-yloxy)methyl)benzoate (1.80 g, 6.3 mmol) in methanol (20 mL) and $CH_2Cl_2$ (20 mL). After 3 d at rt, the reaction mixture was concentrated in vacuo. Water (100 mL) was added and the mixture was extracted with $CH_2Cl_2$ (3×100 mL). The organic phase was washed with brine (100 mL), dried (MgSO$_4$), filtered and concentrated in vacuo. Purification of the crude residue by chromatography on 40 g silica gel (hexanes EtOAc, gradient) afforded 790 mg (49%) of (3-chloro-5-((tetrahydro-2H-pyran-2-yloxy)meth)phenyl) methanol.

Step 3. 3-chloro-5-((tetrahydro-2H-pyran-2-yloxy) methyl)benzaldehyde

DMSO (0.70 mL, 9.06 mmol) was added to a solution of oxalyl chloride (2.0 mL of a 2.0 M solution in CH$_2$Cl$_2$, 4.0 mmol) in CH$_2$Cl$_2$ (3 mL) at −78° C. After 1 h at −78° C., a solution of (3-chloro-5-((tetrahydro-2H-pyran-2-yloxy) methyl)phenyl)methanol (600 mg, 2.33 mmol) in CH$_2$Cl$_2$ (6 mL) was added slowly via syringe. After 5 min at −78° C., triethylamine (2.4 mL, 17.2 mmol) was added and the reaction was allowed to warm to room temperature. After 3 h the reaction mixture was partitioned between saturated aqueous NaHCO$_3$ (50 mL) and CH$_2$Cl$_2$ (150 mL). The phases were separated and the aqueous phase was extracted with CH$_2$Cl$_2$ (2×50 mL). The combined extracts were dried (MgSO$_4$), filtered and concentrated in vacuo to afford of crude 3-chloro-5-((tetrahydro-2H-pyran-2-yloxy)methyl) benzaldehyde, which was used without further purification.

Step 4. (E)-2-(3-chloro-5-(prop-1-enyl)benzyloxy) tetrahydro-2H-pyran

Potassium t-butoxide (1.11 g, 9.89 mmol) was added to a solution of ethyltriphenylphosphonium bromide (2.39 g, 6.44 mmol) in THF (20 mL) at 0° C. To this red/orange mixture was added a solution of crude 3-chloro-5-((tetrahydro-2H-pyran-2-yloxy)methyl)benzaldehyde (~2.33 mmol) in THF (20 mL) at 0° C. After 5 min, the reaction mixture was partitioned between 0.1 N HCl (50 mL) and CH$_2$Cl$_2$ (200 mL). The phases were separated and the aqueous phase was extracted with CH$_2$Cl$_2$ (3×100 mL). The combined organic phase was washed with brine (100 mL), dried (MgSO$_4$), filtered and concentrated in vacuo. Purification of the crude residue by chromatography on 40 g silica gel (hexanes→EtOAc, gradient) afforded 400 mg (64%) of (E)-2-(3-chloro-5-(prop-1-enyl)benzyloxy)tetrahydro-2H-pyran.

Step 5. (E)-(3-chloro-5-(prop-1-enyl)phenyl)methanol

In accordance with the procedure of example 2, step 3, (E)-2-(3-chloro-5-(prop-1-enyl)benzyloxy)tetrahydro-2H-pyran (470 mg, 1.76 mmol) was converted into 240 mg (75%) of (E)-(3-chloro-5-(prop-1-enyl)phenyl)methanol.

Step 6. (E)-1-(bromomethyl)-3-chloro-5-(prop-1-enyl)benzene

Bromine (72 μL, 1.40 mmol) was added to a solution of triphenylphosphine (415 mg, 1.58 mmol) and imidazole (110 mg, 1.62 mmol) in CH$_2$Cl$_2$ (1.5 mL) at 0° C. After 15 min, a solution of (E)-(3-chloro-5-(prop-1-enyl)phenyl) methanol (240 mg, 1.31 mmol) in CH$_2$Cl$_2$ (4.5 mL) was added. After 30 min at 0° C., the reaction mixture was concentrated in vacuo. Purification of the crude residue by chromatography on 40 g silica gel (hexanes→EtOAc, gradient) afforded 240 mg (74%) of (E)-1-(bromomethyl)-3-chloro-5-(prop-1-enyl)benzene.

Step 7. (E)-(3-chloro-5-(prop-1-enyl)benzyl)triphenylphosphonium bromide

In accordance with the procedure of preparation 1, step 5, (E)-1-(bromomethyl)-3-chloro-5-(prop-1-enyl)benzene (240 mg, 0.98 mmol) was converted into 430 mg (87%) of the title compound.

Example 10

5-(3-((1R,2R,3R,5R)-5-chloro-2-((E)-3-chloro-5-((E)-prop-1-enyl)styryl)-3-hydroxycyclopentyl)propyl)thiophene-2-carboxylic acid (15g)

Step 1. Wittig Reaction of 10 to Afford 11g

In accordance with the procedure of example 2, step 2, aldehyde 10 (250 mg, 0.60 mmol) and (E)-(3-chloro-5-(prop-1-enyl)benzyl)triphenylphosphonium bromide (Preparation 7, 430 mg, 0.85 mmol) were converted into 204 mg (60%) of a mixture of alkenes 11g and 12g.

Step 2. Deprotection of 11g and 12g to Give 13g and 14g

In accordance with the procedure of example 2, step 3, THP-ethers 11g and 12g (204 mg, 0.36 mmol) were converted into 107 mg (62%) of alkene 13g and 21 mg (12%) of alkene 14g.

Step 3. Saponification of 13g to Give 15g

In accordance with the procedure of example 2, step 4, ester 13g (49 mg, 0.10 mmol) was converted into 35 mg (74%) of the title compound (15g).

Example 11

5-(3-((1R,2R,3R,5R)-5-chloro-2-((Z)-3-chloro-5-((E)-prop-1-enyl)styryl)-3-hydroxycyclopentyl)propyl)thiophene-2-carboxylic acid (16g)

In accordance with the procedure of example 2, step 4, ester 14g (Example 10, step 2, 21 mg, 0.044 mmol) was converted into 10 mg (49%) of the title compound (16g).

Example 12

5-(3-((1R,2R,3R,5R)-5-chloro-3-hydroxy-2-(3-methylstyryl)cyclopentyl)propyl)thiophene-2-carboxylic acid (15h and 16h)

Step 1. Wittig Reaction of 10 to Afford 11h

In accordance with the procedure of example 2, step 2, aldehyde 10 (250 mg, 0.60 mmol) and (3-methylbenzyl) triphenylphosphonium chloride (483 mg, 1.20 mmol) were converted into 210 mg (69%) of alkene 11h (contaminated with ~10% of cis-alkene 12h).

Step 2. Deprotection of 11h to Give 13h

In accordance with the procedure of example 2, step 3, impure THP-ether 11 h (207 mg, 0.41 mmol) was converted into 166 mg (96%) of alkene 13h (contaminated with ~10% of cis-alkene 14h).

Step 3. Saponification of 13h to Give 15h

In accordance with the procedure of example 2, step 4, impure ester 13h (45 mg, 0.11 mmol) was converted into 5 mg (11%) of the title compound (15h, contaminated with ~10% of cis-alkene 16h).

Preparation 8

((2-Propylpyridin-4-yl)methyl)triphenylphosphonium bromide

Step 1. Methyl 2-propylisonicotinate [In accordance with the procedures of Furstner, et al Angew. Chem. Int. Ed. 2002, 41, 609-612]

At 0° C., n-propylmagnesium chloride (16.0 mL of a 2.0 N solution in THF, 32.0 mmol) was added to a solution of methyl 2-chloroisonicotinate (4.77 g, 27.8 mmol), Fe(acac)$_3$ (610 mg, 1.73 mmol), THF (150 mL) and NMP (17 mL) at 0° C. After 1 h, the reaction was diluted with MTBE (200 mL) and slowly quenched with 1.0 N HCl (20 mL). The mixture was diluted with water (50 mL) and the phases were separated. The aqueous phase was extracted with MTBE (2×200 mL). The combined organic phase was dried (MgSO$_4$), filtered and concentrated in vacuo. Purification of the crude residue by flash column chromatography on 200 g silica gel (20% hexanes/EtOAc) afforded 2.3 g (46%) of methyl 2-propylisonicotinate.

Step 2. (2-propylpyridin-4-yl)methanol

In accordance with the procedures of preparation 6, step 1, methyl 2-propylisonicotinate (2.15 g, 12.0 mmol) was converted into 1.2 g (66%) of (2-propylpyridin-4-yl)methanol.

Step 3. 4-(bromomethyl)-2-propylpyridine

In accordance with the procedures of preparation 7, step 6, (2-propylpyridin-4-yl)methanol (700 mg, 4.63 mmol) was converted into 600 mg (61%) of 4-(bromomethyl)-2-propylpyridine.

Step 4. ((2-Propylpyridin-4-yl)methyl)triphenylphosphonium bromide

In accordance with the procedure of preparation 1, step 5, 4-(bromomethyl)-2-propylpyridine (350 mg, 1.64 mmol) was converted into 710 mg (91%) of the title compound.

Example 13

5-(3-((1R,2R,3R,5R)-5-chloro-3-hydroxy-2-((E)-2-(2-propylpyridin-4-yl)vinyl)cyclopentyl)propyl)thiophene-2-carboxylic acid (15i)

Step 1. Wittig Reaction of 10 to Afford 11i

In accordance with the procedure of example 2, step 2, aldehyde 10 (250 mg, 0.60 mmol) and ((2-propylpyridin-4-yl)methyl)triphenylphosphonium bromide (430 mg, 0.90 mmol) were converted into 250 mg (78%) of a alkene 11i (contaminated with ~10% of cis-alkene 12i).

Step 2. Deprotection of 11i to Give 13i

In accordance with the procedure of example 2, step 3, impure THP-ether 11i (250 mg, 0.47 mmol) was converted into 201 mg (95%) of alkene 13i (contaminated with ~10% of cis-alkene 14i).

Step 3. Saponification of 13i to Give 15i

In accordance with the procedure of example 2, step 4, impure ester 13i (20 mg, 0.045 mmol) was converted into 8 mg (41%) of the title compound (15i, contaminated with ~10% of cis-alkene 16i).

Scheme 3

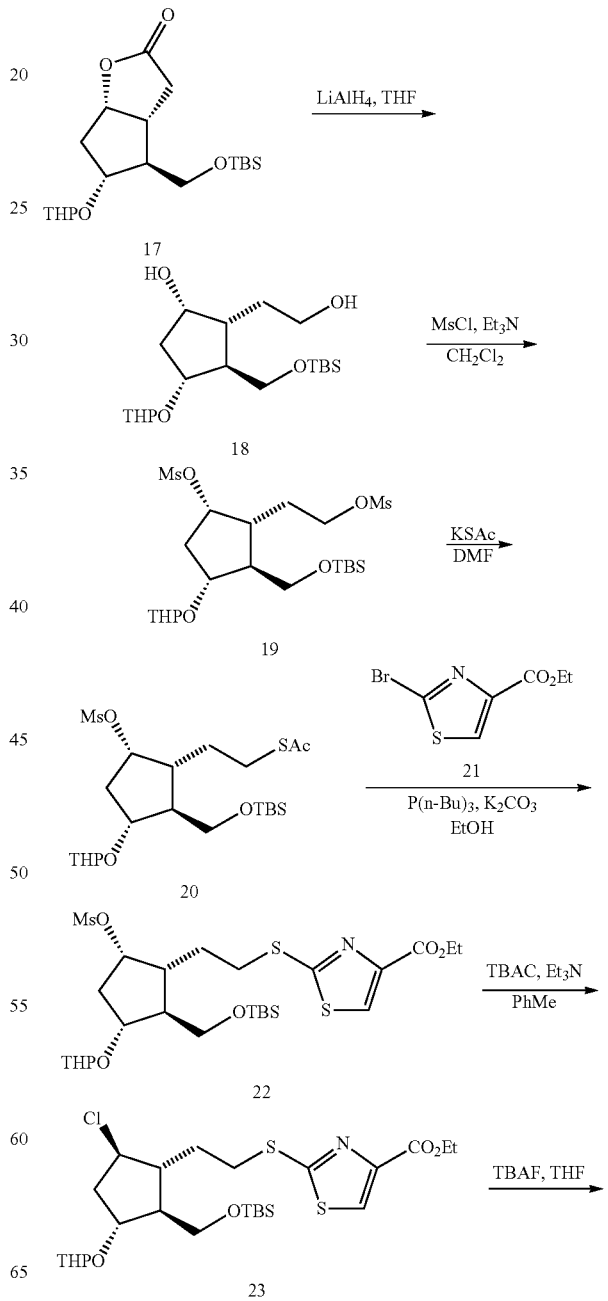

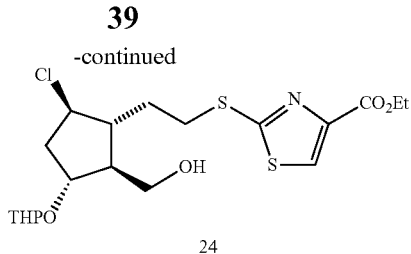

24

Preparation 9 ethyl 2-(2-((1R,2S,3R,5R)-5-chloro-2-(hydroxymethyl)-3-(tetrahydro-2H-pyran-2-yloxy)cyclopentyl)ethylthio)thiazole-4-carboxylate (24)

Step 1. Reduction of Lactone 17 to Diol 18

LiAlH$_4$ (13.5 mL of a 1.0 M solution in THF, 13.5 mmol) was slowly added to a solution of lactone 17 (5.0 g, 13.5 mmol) in THF (45 mL) at 0° C. under nitrogen (vigorous gas evolution was observed). After 3 h at 0° C., tlc analysis showed the reaction was complete and water (50 mL) was added slowly. Upon warming to rt, CH$_2$Cl$_2$ (250 mL) was added, followed by 15% aqueous NaOH (100 mL). The phases were separated and the aqueous phase was extracted CH$_2$Cl$_2$ (3×100 mL). The combined organic phase was washed with brine, dried (MgSO$_4$), filtered and concentrated in vacuo. The resulting crude diol 18 (~5g) was used in the next reaction with out further purification.

Step 2. Mesylation of Diol 18 to Afford Di-Mesylate 19

Triethylamine (4.4 mL, 31.6 mmol) and methanesulfonyl chloride (1.8 mL, 23.2 mmol) were added sequentially to a solution of 18 (3.57 g, 9.53 mmol) in CH$_2$Cl$_2$ (100 mL) at 0° C. The reaction mixture was allowed to warm to rt and stirred at rt for 3 d (note: this reaction time can be as short as 1d). Saturated aqueous NaHCO$_3$ (100 mL) was added and the mixture was extracted with CH$_2$Cl$_2$ (300 mL). The organic phase was washed with brine (50 mL) then dried (MgSO$_4$), filtered and concentrated in vacuo. Purification of the crude residue by flash column chromatography on 80g silica gel (hexane→EtOAc, gradient) afforded 4.44 g (88%) of di-mesylate 19.

Step 3. Conversion of Mesylate 19 to Thioacetate 20

Potassium thioacetate (1.51 g, 13.2 mmol) was added to a solution of di-mesylate 19 (4.44 g, 8.37 mmol) in DMF (100 mL) at rt. After stirring 18 h at rt, the mixture was partitioned between EtOAc (400 mL) and water (50 mL). The phases were separated and the organic phase was washed with water (10×100 mL), dried (MgSO$_4$), filtered and concentrated in vacuo. Purification of the crude residue by traditional flash column chromatography on silica gel (30% EtOAc/hexanes) afforded 2.93 g (69%) of thioacetate 20.

Step 4. Reaction of 20 with 21 to Give Thiazole 22

Tri-n-butylphosphine (0.25 mL, 1.0 mmol) was added to a solution of thioacetate 20 (2.42 g, 4.74 mmol) in absolute EtOH (20 mL). After 5 min at rt under nitrogen, ethyl 2-bromothiazole-4-carboxylate (21, commercially available from CombiBlocks, Inc., 1.30 g, 5.51 mmol) and potassium carbonate (1.09 g, 7.89 mmol) were added in rapid succession. A nitrogen atmosphere was re-established and mixture was heated at 40° C. overnight. The mixture was cooled to rt and then partitioned between EtOAc (700 mL) and water (200 mL). The phases were separated and the organic phase was washed with brine (100 mL), dried (MgSO$_4$), filtered and concentrated in vacuo. Purification of the crude residue by flash column chromatography on 80g silica gel (hexane→EtOAc, gradient) afforded 1.10 g (37%) of thiazole 22.

Step 5. Conversion of Mesylate 22 to Chloride 23

Triethylamine (2.5 mL, 17.9 mmol) and tetrabutylammonium chloride (2.5 g, 9.0 mmol) were added to a solution of 22 (1.10 g, 1.76 mmol) in toluene (20 mL). The reaction mixture was heated at 40° C. for 18 h. TLC analysis of the cooled mixture showed the reaction to be incomplete. More triethylamine (1.2 mL, 8.6 mmol) and tetrabutylammonium chloride (1.2 g, 4.3 mmol) were added and the mixture was heated at 40° C. for 18 h. The cooled mixture was diluted with water (100 mL) and extracted with EtOAc (300 mL). The organic phase was washed with brine (50 mL), dried (MgSO$_4$), filtered and concentrated in vacuo. Purification of the crude residue by flash column chromatography on 40g silica gel (hexane→EtOAc, gradient) afforded 720 mg (72%) of chloride 23.

Step 6. Desilylation of 23 to Give Alcohol 24

Tetrabutylammonium fluoride (1.8 mL of a 1.0 M solution in THF, 1.8 mmol) was added to a solution of 23 (720 mg, 1.28 mmol) in THF (7 mL) at rt. After 1 h at rt, the reaction mixture was partitioned between EtOAc (200 mL) and H$_2$O (100 mL). The phases were separated and the organic phase was washed with brine (2×50 mL) then dried (MgSO$_4$), filtered and concentrated in vacuo. Purification of the crude residue by flash column chromatography on 12g silica gel (hexane→EtOAc, gradient) afforded 510 mg (89%) of the title compound (24).

Scheme 4

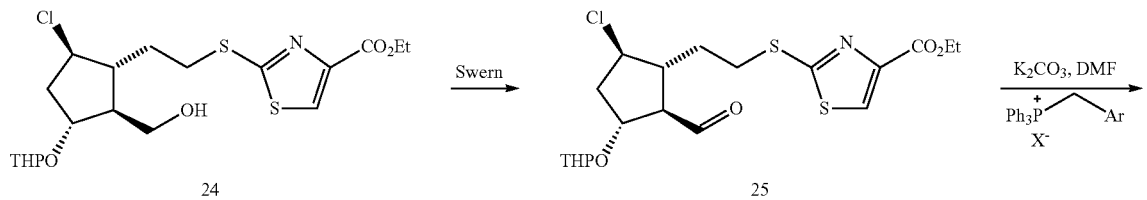

-continued

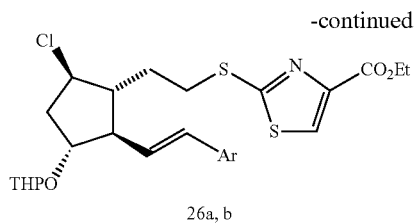

26a, b

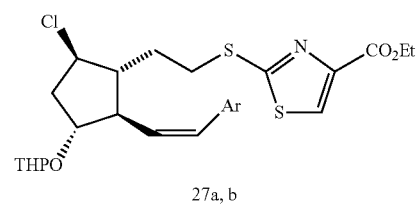

27a, b

↓ PPTs, MeOH

↓ PPTs, MeOH

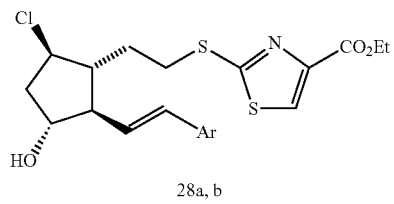

28a, b

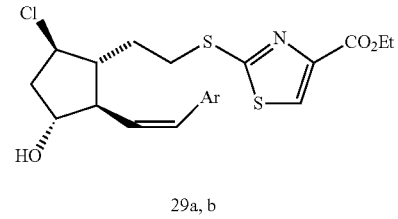

29a, b

↓ LiOH, H₂O, THF

↓ LiOH, H₂O, THF

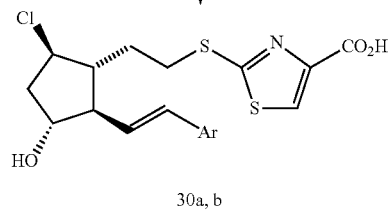

30a, b

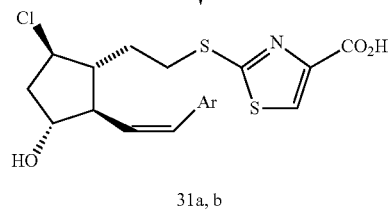

31a, b

Example 14

2-(2-((1R,2R,3R,5R)-5-chloro-2-(3,5-dichlorostyryl)-3-hydroxycyclopentyl)ethylthio)thiazole-4-carboxylic acid (30a)

Step 1. Swern Oxidation of 24 to Give 25

In accordance with the procedure of example 2, step 1, alcohol 24 (Preparation 9, 150 mg, 0.34 mmol) was converted into crude aldehyde 25 which was used without further purification in the next step.

Step 2. Wittig Reaction of 25 to Afford 26a and 27a

In accordance with the procedure of example 2, step 2, aldehyde 24 (~0.17 mmol) and 3,5-dichlorophenylmethyltriphenylphosphonium chloride (210 mg, 0.46 mmol) were converted into 91 mg (33%) of an inseparable mixture of alkenes 26a and 27a.

Step 3. Deprotection of 26a and 27a to Give 28a and 29a

In accordance with the procedure of example 2, step 3, THP-ethers 26a and 27a (91 mg, 0.15 mmol) were converted into 40 mg (51%) of alkene 28a and 21 mg (27%) of alkene 29a.

Step 4. Saponification of 28a to Give 30a

In accordance with the procedure of example 2, step 4, ester 28a (10 mg, 0.020 mmol) was converted into 2 mg (21%) of the title compound (30a).

Example 15

2-(2-((1R,2R,3R,5R)-2-((E)-3-(but-3-enyl)-5-chlorostyryl)-5-chloro-3-hydroxycyclopentyl)ethylthio)thiazole-4-carboxylic acid (30b)

Step 1. Wittig Reaction of 25 to Afford 26b and 27b

In accordance with the procedure of example 2, step 2, aldehyde 25 (141 mg, 0.31 mmol) and 3-(but-3-enyl)phenyl)methyl)triphenylphosphonium chloride (Preparation 6, 317 mg, 0.72 mmol) were converted into 105 mg (58%) of a mixture of alkenes 26b and 27b.

Step 2. Deprotection of 26b and 27b to Give 28b and 29b

In accordance with the procedure of example 2, step 3, THP-ethers 26b and 27b (105 mg, 0.18 mmol) was converted into 67 mg (75%) of alkene 28b and 12 mg (13%) of alkene 29b.

Step 3. Saponification of 28b to Give 30b

In accordance with the procedure of example 2, step 4, ester 28b (67 mg, 0.14 mmol) was converted into 30 mg (47%) of the title compound (30b).

Example 16

2-(2-((1R,2R,3R,5R)-2-(Z)-3-(but-3-enyl)-5-chlorostyryl)-5-chloro-3-hydroxycyclopentyl)ethylthio)thiazole-4-carboxylic acid (31b)

In accordance with the procedure of example 2, step 4, ester 29b (12 mg, 0.24 mmol) was converted into 5 mg (44%) of the title compound (31b).

Example 17

5-(3-((1R,2S,3R)-3-hydroxy-5-oxo-2-(phenylethynyl)cyclopentyl)propyl)thiophene-2-carboxylic acid (38)

Step 1. Conjugate Addition and Silylation to Afford 33

Trimethylaluminum (4.1 mL of a 2.0 M solution in toluene, 8.2 mmol) was added to a flask containing THF (20 mL), and the flask was cooled to −78° C. Lithium phenylacetylide (8.2 mL of a 1.0 M solution in THF, 8.2 mmol) was added and the reaction was stirred for 30 min at −78° C. Another flask was charged with enone 32 (see WO2007/

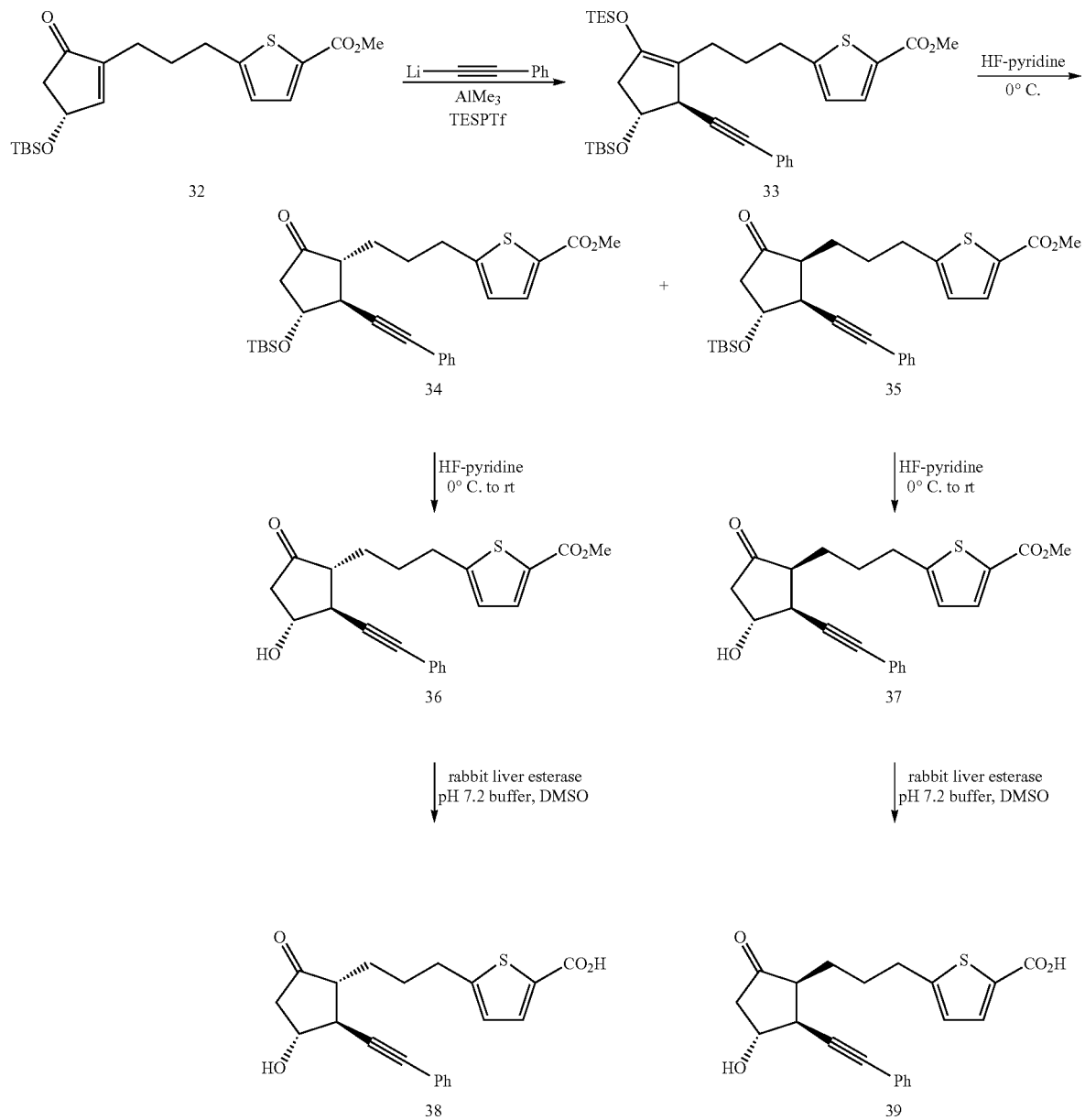

115020 which is hereby incorporated by reference in itsentirety) in THF (20 mL), cooled to −78° C., and TESOTf (1.80 g, 6.81 mmol) was added (it is important to cool the enone to −78° C. prior to TESOTf addition). After having stirred for 30 min at −78° C., the contents of the aluminum containing flask were transferred via cannula to the second flask (containing the enone) at −78° C., and the reaction was allowed to stir for 30 min. The reaction was warmed to approximately −10° C. and saturated aqueous Rochelle's Salt (200 mL) was added (5 min after quenching, the reaction effervesced; the final flask must be large enough to allow for this action). Robust stirring of the contents continued for several hours and the contents were transferred to a separatory funnel and were washed once with $Et_2O$ and $CH_2Cl_2$. The combined organic phase was dried ($Na_2SO_4$) and combiflash chromatography provided 1.20 g of pure product, and 784 mg of product contaminated with 5% ketone (~75%).

Step 2. Deprotection of 33 to Give 34 and 35

Silyl enol ether 33 (260 mg, 0.43 mmol) and MeCN (10 mL) were added to a plastic bottle and cooled to 0° C. HF.pyridine (0.05 mL) was added and the reaction was stirred for 2 h at 0° C. The reaction was then quenched slowly with saturated aqueous $NaHCO_3$, and the mixture was extracted once with EtOAc and once with $CH_2Cl_2$. The combined organic phase was dried ($Na_2SO_4$), concentrated and Combiflash chromatography gave 75 mg (35%) of ketone 34 followed by followed by 28.7 mg (14%) of the slower moving isomer ketone 35.

Step 3. Deprotection of 34 to Give 36

Silyl ether 34 (75 mg, 0.15 mmol) and MeCN (3 mL) were added to a plastic vial and cooled to 0° C. HF.pyridine (0.05 mL) was added and the reaction was allowed to warm to room temperature overnight with stirring. The reaction was then quenched slowly with saturated aqueous $NaHCO_3$, and the mixture was extracted once with EtOAc and once with $CH_2Cl_2$. The combined organic phase was dried ($Na_2SO_4$), concentrated and Combiflash chromatography gave 45.6 mg (79%) of ketone 36.

Step 4. Saponification of 36 to Give 38

Ester 36 (10 mg, 0.026 mmol), DMSO (0.5 mL), and pH 7.2 phosphate buffer (50 mL) were added to a 100 mL round bottomed flask followed by the addition of rabbit liver esterase (RLE, commercially available from Sigma, 500 units). After having stirred for 12 h at room temperature, the reaction was concentrated in vacuo. Purification of the crude residue by flash column chromatography (50% EtOAc/hexanes→1% AcOH in EtOAc) afforded 7.3 mg (76%) of the title compound (38).

Example 18

5-(3-((1S,2S,3R)-3-hydroxy-5-oxo-2-(phenylethynyl)cyclopentyl)propyl)thiophene-2-carboxylic acid (39)

Step 1. Deprotection of 35 to Give 37

In accordance with the procedure of example 17, step 3, silyl ether 35 (28.7 mg, 0.058 mmol) was converted to 17.1 mg (77%) of ketone 37.

Step 4. Saponification of 37 to Give 39

In accordance with the procedure of example 17, step 4, ester 37 (17.1 mg, 0.045 mmol) was converted to 14.4 mg (87%) of the title compound (39).

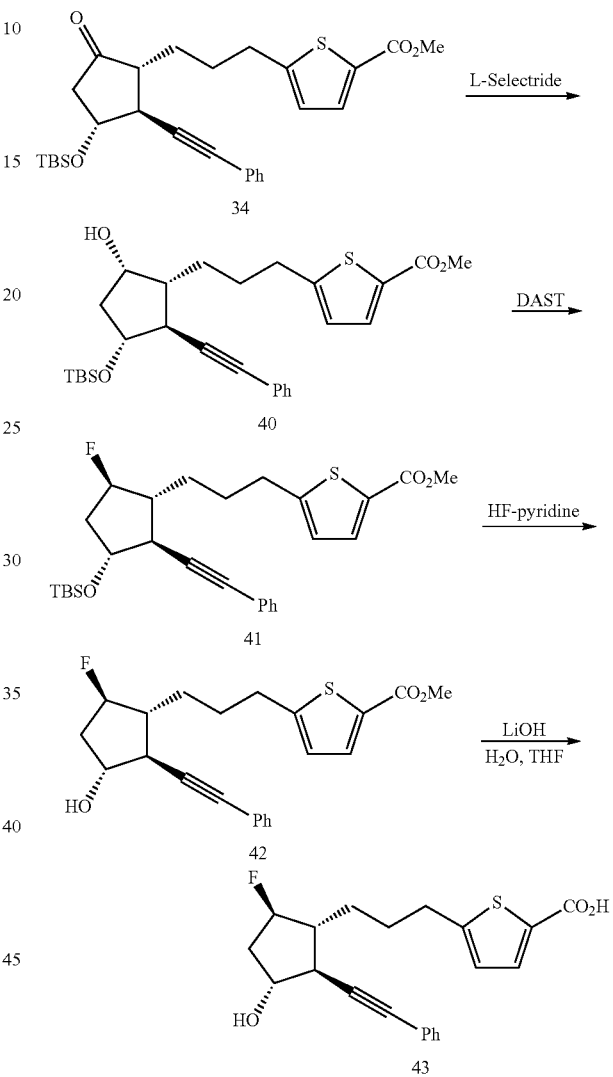

Example 19

5-(3-((1R,2S,3R,5R)-5-fluoro-3-hydroxy-2-(phenylethynyl)cyclopentyl)propyl)thiophene-2-carboxylic acid (43)

Step 1. Reduction of 34 to Give 40

L-Selectride (1.14 mL of a 1.0 M solution in THF, 1.14 mmol) was added to a solution of ketone 34 (170 mg, 0.34 mmol) in THF (5 mL) at −78° C. After 1 h, 3% $H_2O_2$ (25 mL) was added and the reaction was warmed to room temperature. After 0.5 h of stirring at room temperature, saturated aqueous $NH_4Cl$ was added and the mixture was extracted with EtOAc (3×). The combined organic phase was washed with brine, dried (Na$_2$SO$_4$), and concentrated. Purification of the crude residue by flash column chromatography afforded 150 mg (88%) of the desired alcohol 40.

Step 2. Conversion of Alcohol 40 to Fluoride 41

(Diethylamino)sulfur trifluoride (DAST, 17 µL, 0.13 mmol) was added to a solution of alcohol 40 (30 mg, 0.060 mmol) in CH$_2$Cl$_2$ (3 mL) at −78° C. After stirring for 30 min, the mixture was diluted with water, extracted with CH$_2$Cl$_2$ (3×) and hexanes (1×). The combined organic phase was washed with brine, dried (Na$_2$SO$_4$), and concentrated. Purification of the crude residue by combiflash chromatography afforded 23 mg (76%) of fluoride 41.

Step 3. Deprotection of 41 to Give 42

HF.pyridine (0.15 mL) was added to a solution of 41 (23 mg, 0.046 mmol) in MeCN (2 mL) in a plastic vial. After stirring 16 h, the mixture was quenched with saturated aqueous NaHCO$_3$ and extracted with EtOAc.

The organic phase was washed with brine, dried (Na$_2$SO$_4$), filtered and concentrated in vacuo. Purification of the crude residue by combiflash chromatography afforded 16 mg (90%) of alcohol 42.

Step 4. Saponification of 42 to Give 43

Lithium hydroxide (6.5 mg, 0155 mmol) was added to a solution of ester 11 (8 mg, 0.021 mmol) in a 1:0.5 THF/water solution (1.5 mL). After having stirred 72 h, purification of the residue by flash column chromatography provided 8 mg (quant.) of the title compound (43).

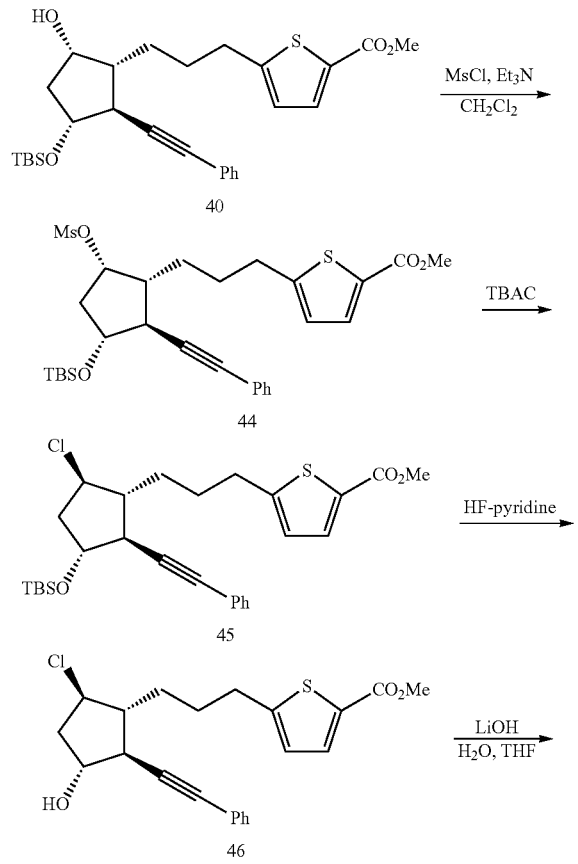

Scheme 7

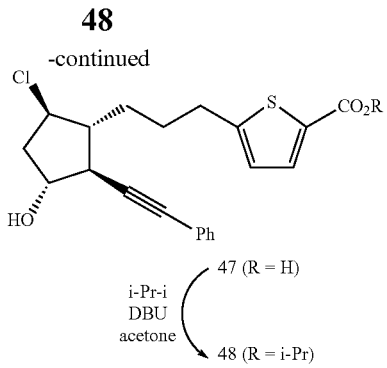

Example 20

5-(3-((1R,2S,3R,5R)-5-chloro-3-hydroxy-2-(phenylethynyl)cyclopentyl)propyl)thiophene-2-carboxylic acid (47)

Step 1. Mesylation of 40 to Give 44

Methanesulfonyl chloride (37 µL, 0.48 mmol) was added to a solution of alcohol 40 (120 mg, 0.24 mmol) and triethylamine (0.10 mL, 0.72 mmol) in CH$_2$Cl$_2$ (3 mL). After stirring 1 hour at room temperature, the mixture was quenched with saturated aqueous NaHCO$_3$. The organic phase was separated and washed with brine, dried (Na$_2$SO$_4$), filtered and concentrated. Purification of the crude residue by flash column chromatography provided 110 mg (79%) of mesylate 44.

Step 2. Conversion of Mesylate 44 to Chloride 45

TBAC (245 mg, 0.88 mmol) was added to a solution of mesylate 44 (50 mg, 0.087 mmol) in toluene (2 mL) and the mixture was then stirred at 45° C. for 6 h. The mixture was then cooled to room temperature and water was added. The aqueous layer was extracted with EtOAc, and the organic phase was washed with brine, dried (Na$_2$SO$_4$), filtered and concentrated. Purification of the crude residue by combiflash chromatography provided 45 mg (quant.) of chloride 45.

Step 3. Deprotection of 45 to Give 46

In accordance with the procedure of example 19, step 3, silyl ether 45 (45 mg, 0.087 mmol) was converted to 31 mg (89%) of alcohol 46.

Step 4. Saponification of 46 to Give 47

In accordance with the procedure of example 19, step 4, ester 46 (31 mg, 0.077 mmol) was converted to 15.8 mg (53%) of the title compound (47).

Example 21

Isopropyl 5-(3-((1R,2S,3R,5R)-5-chloro-3-hydroxy-2-(phenylethynyl)cyclopentyl)propyl)thiophene-2-carboxylate (48)

2-Iodopropane (passed through a short column of activated basic, Brockman I, standard grade, 150 mesh Alumina just prior to use, 43 mg, 0.26 mmol) was added to a mixture of acid 47 (5 mg, 0.013 mmol) and DBU (7.8 mg, 0.051 mmol) in acetone (0.4 mL). After stirring for 16 h, the mixture was concentrated, extracted with EtOAc. The organic phase was washed with 1% aqueous HCl, saturated aqueous NaHCO₃, brine, then dried (Na₂SO₄), filtered and concentrated in vacuo. Purification of the crude residue by combiflash chromatography afforded 2.9 mg (52%) of the title compound (48).

Step 3. Saponification of 50 to Give 51

In accordance with the procedure of example 19, step 4, ester 50 (7.3 mg, 0.019 mmol) was converted to 5 mg (71%) of the title compound (51).

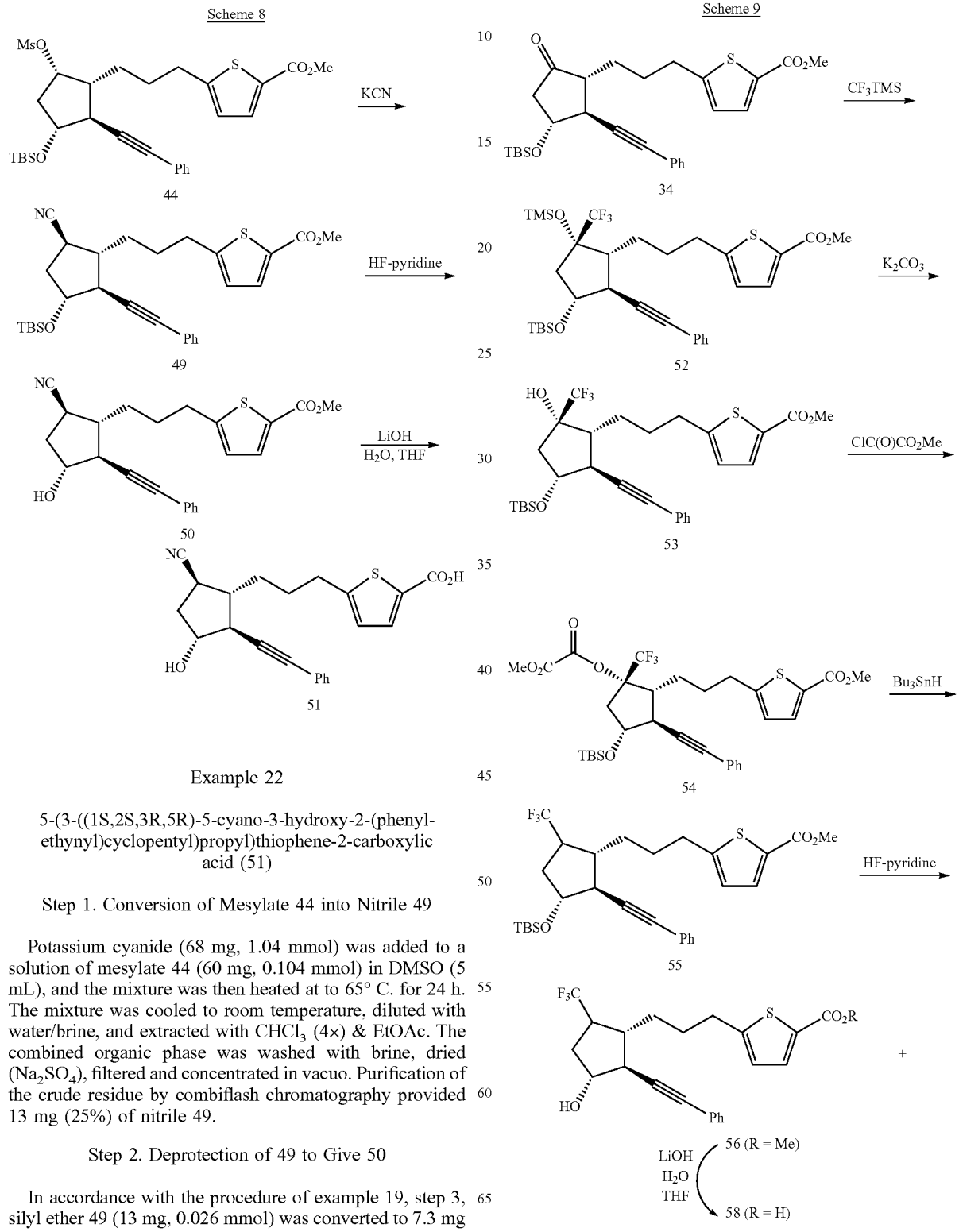

Example 22

5-(3-((1S,2S,3R,5R)-5-cyano-3-hydroxy-2-(phenyl-ethynyl)cyclopentyl)propyl)thiophene-2-carboxylic acid (51)

Step 1. Conversion of Mesylate 44 into Nitrile 49

Potassium cyanide (68 mg, 1.04 mmol) was added to a solution of mesylate 44 (60 mg, 0.104 mmol) in DMSO (5 mL), and the mixture was then heated at to 65° C. for 24 h. The mixture was cooled to room temperature, diluted with water/brine, and extracted with CHCl₃ (4×) & EtOAc. The combined organic phase was washed with brine, dried (Na₂SO₄), filtered and concentrated in vacuo. Purification of the crude residue by combiflash chromatography provided 13 mg (25%) of nitrile 49.

Step 2. Deprotection of 49 to Give 50

In accordance with the procedure of example 19, step 3, silyl ether 49 (13 mg, 0.026 mmol) was converted to 7.3 mg (72%) of alcohol 50.

-continued

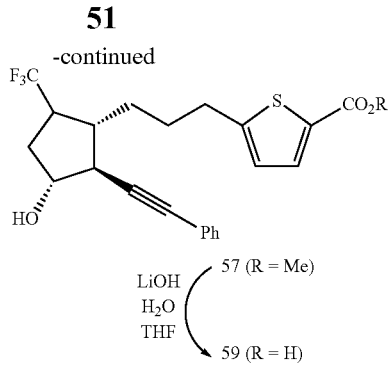

57 (R = Me)
LiOH
H₂O
THF
59 (R = H)

Example 23

5-(3-((1R,2S,3R)-3-hydroxy-2-(phenylethynyl)-5-(trifluoromethyl)cyclopentyl)propyl)thiophene-2-carboxylic add (faster eluting HPLC diastereomer 58)

Step 1. Conversion of 34 into 52

Trifluoromethyl trimethylsilane (Fluka, 8 mL of a 2.0 M solution in THF, 16 mmol) was added to a solution of ketone 34 (300 mg, 0.60 mmol) in THF (17 mL) at room temperature, followed by the addition of 4 drops of tetrabutylammonium fluoride (TBAF, 1.0 M in THF); the reaction turned light yellow. After 45 min, the reaction was quenched slowly with saturated aqueous $NH_4Cl$ and extracted with EtOAc (3×). The combined organic phase was washed with brine, dried ($Na_2SO_4$), filtered and concentrated. The crude silane 52 was dried under high vacuum for 12 hours prior to the following reaction.

Step 2. Desilylation of 52 to Give 53

Solid $K_2CO_3$ (248 mg, 1.79 mmol) was added to crude silane 52 in MeOH (40 mL) and the mixture was stirred for 4 h. The reaction was then diluted with saturated aqueous $NH_4Cl$, and extracted with EtOAc, The organic phase was washed with brine, dried ($Na_2SO_4$), filtered and concentrated. Purification of the crude residue by combiflash chromatography afforded 170 mg (50% over two steps) of alcohol 53.

Step 3. Conversion of Alcohol 53 into Ester 54

Methyl oxalyl chloride (183 mg, 1.49 mmol) was added slowly to a mixture of alcohol 53 (170 mg, 0.30 mmol), pyridine (0.73 mL, 9.0 mmol), 4-N,N-dimethylaminopyridine (220 mg, 1.80 mmol), and $CH_2Cl_2$ (8 mL). After stirring 1.5 h, the mixture was quenched with water, diluted with EtOAc/hexanes (4:1; 20 mL), and partitioned. The organic phase was washed again with water (20 mL), then dried ($Na_2SO_4$), filtered and concentrated in vacuo. Purification of the crude residue by combiflash chromatography afforded 162 mg (83%) of ester 54.

Step 4. Conversion of Ester 54 into 55

A mixture of oxalyl ester 54 (162 mg, 025 mmol), AlBN (40 mg) and toluene (2 mL) was bubbled with nitrogen gas for 20 min. Separately, a solution of $Bu_3SnH$ (727 mg, 2.50 mmol) in toluene (10 mL) was bubbled with nitrogen gas for 20 min, and then brought to 120° C. The AlBN containing mixture was quickly added dropwise. After 20 min, TLC indicated no starting material and the reaction was concentrated to afford 129 mg (~94%) of crude 55.

Step 5. Deprotection of 55 to Give 56 and 57

In accordance with the procedure of example 19, step 3, crude silyl ether 55 (129 mg, ~0.234 mmol) was converted to 4 mg (4%) of faster eluting alcohol 56 and 10.4 mg (10%) of slower eluting alcohol 57 after HPLC separation (EtOAc/hex; 1:3).

Step 6. Saponification of 56 to Give 58

In accordance with the procedure of example 19, step 4, ester 56 (4 mg, 0.009 mmol) was converted to 2.2 mg (57%) of the title compound (58).

Example 24

5-(3-((1R,2S,3R)-3-hydroxy-2-(phenylethynyl)-5-(trifluoromethyl)cyclopentyl)propyl)thiophene-2-carboxylic acid (slower eluting HPLC diastereomer 59)

In accordance with the procedure of example 19, step 4, ester 57 (10.4 mg, 0.024 mmol) was converted to 5 mg (50%) of the title compound (59).

Scheme 10

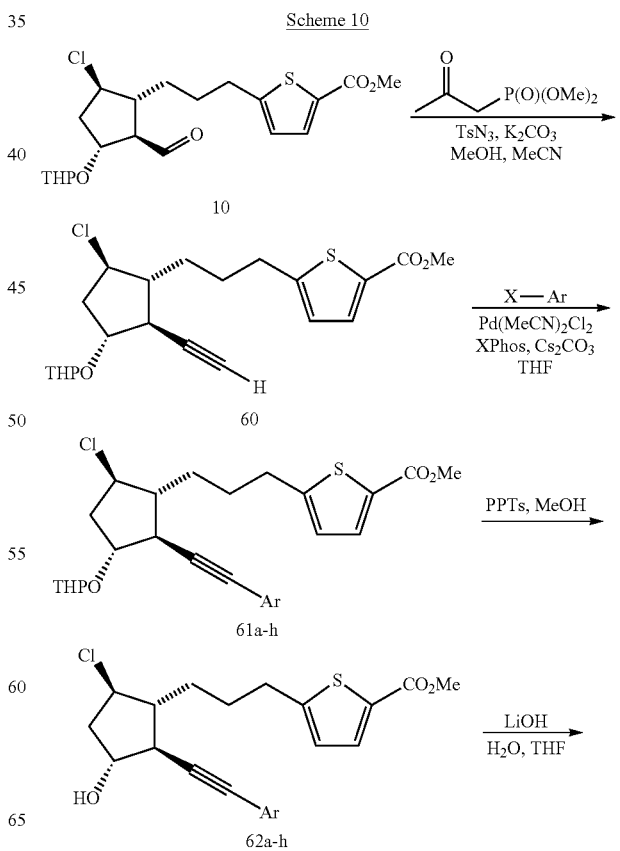

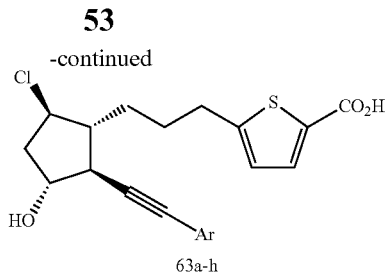

63a-h

Example 25

5-(3-((1R,2S,3R,5R)-5-chloro-2-((3,5-dichlorophenyl)ethynyl)-3-hydroxycyclopentyl)propyl)thiophene-2-carboxylic acid (63a)

Step 1. Reaction of 10 to Give 60 (in Accordance with the Procedures of Roth, et al., *Synthesis* 2004, 59-62)

To a mixture of tosyl azide (240 mg, 1.22 mmol) and potassium carbonate (415 mg, 3.0 mmol) in MeCN (15 mL) was added dimethyl-2-oxopropylphosphonate (166 µL, 1.20 mmol). After 2 h of stirring at room temperature, a solution of crude aldehyde 10 (prepared in accordance with the procedure of example 2, step 1, ~1.0 mmol) in MeOH (3 mL) was added by cannula. The mixture was allowed to stir overnight at room temperature then was concentrated in vacuo. Water (10 mL) was added and the mixture was extracted with EtOAc (20 mL). The organic phase was washed with water (10 mL) and brine (10 mL), then dried (Na$_2$SO$_4$), filtered and concentrated in vacuo. Purification of the crude residue by chromatography on 40g silica gel (hexanes→EtOAc, gradient) afforded 203 mg (49%, slightly contaminated with tosyl amide) of alkyne 60.

Step 2. Arylation of 60 to Give 61a (in Accordance with the Procedures of Gelman and Buchwald, Angew. *Chem. Int. Ed.* 2003, 42, 5993-5996)

Cesium carbonate (80 mg, 0.25 mmol), bis(acetonitrile) palladium (II) chloride (1.6 mg, 0.006 mmol), 2-dicyclohexylphosphino-2',4',6-triisopropylbiphenyl (XPhos, 8.8 mg, 0.018 mmol) and 1-bromo-3,5-dichlorobenzene (27.5 mg, 0.12 mmol) were combined in a 1 dram vial. The mixture was purged with nitrogen, stirred at room temperature for 25 min, then a solution of alkyne 60 (50 mg, 0.12 mmol) in MeCN (0.25 mL) was added. After 3 h at room temperature, tlc analysis showed very little reaction had occurred so the vial was sealed under nitrogen and heated at 50° C. After 18 h, the mixture was cooled, diluted with EtOAc and filtered through celite. The filtrate was concentrated in vacuo. Purification of the crude residue by chromatography on 12g silica gel (hexanes→EtOAc, gradient) afforded 34.5 mg (51%) of 61a.

Step 3. Deprotection of 61a to Give 62a

In accordance with the procedures of example 2, step 3, THP-ether 61a (34 mg, 0.061 mmol) was converted into 25 mg (87%) of alcohol 62a.

Step 4. Saponification of 62a to Give 63a

In accordance with the procedures of example 4, step 3, ester 62a (25 mg, 0.053 mmol) was converted into 16.5 mg (68%) of the title compound (63a).

Example 26

5-(3-((1R,2S,3R,5R)-5-chloro-2-((3-ethylphenyl)ethynyl)-3-hydroxycyclopentyl)propyl)thiophene-2-carboxylic acid (63b)

Step 1. Arylation of 60 to Give 61b

In accordance with the procedures of example 24, step 2, 60 (50 mg, 0.12 mmol) and 1-bromo-3-ethylbenzene (26 mg, 0.14 mmol) were converted into 41 mg (65%) of 61b after heating at 70° C. for 4 h.

Step 2. Deprotection of 61b to Give 62b

In accordance with the procedures of example 2, step 3, THP-ether 61b (41 mg, 0.080 mmol) was converted into 30 mg (87%) of alcohol 62b.

Step 3. Saponification of 62b to Give 63b

In accordance with the procedures of example 4, step 3, ester 62b (30 mg, 0.070 mmol) was converted into 27 mg (93%) of the title compound (63b) after heating at 40° C. for 18 h.

Example 27

5-(3-((1R,2S,3R,5R)-2-((3-(but-3-enyl)phenyl)ethynyl)-5-chloro-3-hydroxycyclopentyl)propyl)thiophene-2-carboxylic acid (63c)

Step 1. Arylation of 60 to Give 61c

In accordance with the procedures of example 24, step 2, 60 (36 mg, 0.088 mmol) and 1-bromo-3-(but-3-enyl)benzene (18.5 mg, 0.088 mmol) were converted into 42 mg (89%) of 61c after heating at 50° C. for 18 h.

Step 2. Deprotection of 61c to Give 62c

In accordance with the procedures of example 2, step 3, THP-ether 61c (42 mg, 0.078 mmol) was converted into 24 mg (68%) of alcohol 62c.

Step 3. Saponification of 62c to Give 63c

In accordance with the procedures of example 4, step 3, ester 62c (24 mg, 0.070 mmol) was converted into 16 mg (69%) of the title compound (63c) after heating at 40° C. for 18 h.

Example 28

5-(3-((1R,2S,3R,5R)-5-chloro-3-hydroxy-2-(thiophen-2-ylethynyl)cyclopentyl)propyl)thiophene-2-carboxylic add (63d)

Step 1. Arylation of 60 to Give 61d

In accordance with the procedures of example 24, step 2, 60 (65 mg, 0.16 mmol) and 2-chlorothiophene (15 µL, 0.16 mmol) were converted into 15 mg (19%) of 61d after heating at 50° C. for 18 h.

Step 2. Deprotection of 61d to Give 62d

In accordance with the procedures of example 2, step 3, THP-ether 61d (15 mg, 0.030 mmol) was converted into 10 mg (80%) of alcohol 62d.

Step 3. Saponification of 62d to Give 63d

In accordance with the procedures of example 4, step 3, ester 62d (5 mg, 0.012 mmol) was converted into 2 mg (41%) of the title compound (63d) after heating at 40° C. for 18 h and purification by preparative thin layer chromatography eluting with 20% MeOH/CH$_2$Cl$_2$.

Example 29

5-(3-((1R,2S,3R,5R)-5-chloro-3-hydroxy-2-(thiophen-3-ylethynyl)cyclopentyl)propyl)thiophene-2-carboxylic add (63e)

Step 1. Arylation of 60 to Give 61e

In accordance with the procedures of example 24, step 2, 60 (65 mg, 0.16 mmol) and 3-chlorothiophene (15 µL, 0.16 mmol) were converted into 25 mg (32%) of 61e after heating at 50° C. for 18 h.

Step 2. Deprotection of 61e to Give 62e

In accordance with the procedures of example 2, step 3, THP-ether 61e (25 mg, 0.051 mmol) was converted into 20 mg (96%) of alcohol 62e.

Step 3. Saponification of 62e to Give 63e

In accordance with the procedures of example 4, step 3, ester 62e (10 mg, 0.024 mmol) was converted into 1 mg (10%) of the title compound (63e) after heating at 40° C. for 18 h and purification by preparative thin layer chromatography eluting with 20% MeOH/CH$_2$Cl$_2$.

Example 30

5-(3-((1R,2S,3R,5R)-5-chloro-3-hydroxy-2-(pyridin-2-ylethynyl)cyclopentyl)propyl)thiophene-2-carboxylic acid (63f)

Step 1. Arylation of 60 to Give 61f

In accordance with the procedures of example 24, step 2, 60 (107 mg, 0.26 mmol) and 2-bromopyridine (50 µL, 0.52 mmol) were converted into 74 mg (58%) of 61f after heating at 60° C. for 18 h.

Step 2. Deprotection of 61f to Give 62f

In accordance with the procedures of example 2, step 3, THP-ether 61f (74 mg, 0.15 mmol) was converted into 22 mg (36%) of alcohol 62f.

Step 3. Saponification of 62f to Give 63f

In accordance with the procedures of example 4, step 3, ester 62f (10 mg, 0.025 mmol) was converted into 5 mg (52%) of the title compound (63f) after purification by preparative thin layer chromatography eluting with 30% MeOH/CH$_2$Cl$_2$.

Example 31

5-(3-((1R,2S,3R,5R)-5-chloro-3-hydroxy-2-(pyridin-3-ylethynyl)cyclopentyl)propyl)thiophene-2-carboxylic acid (63 g)

Step 1. Arylation of 60 to Give 61g

In accordance with the procedures of example 24, step 2, 60 (150 mg, 0.37 mmol) and 3-bromopyridine (116 mg, 0.73 mmol) were converted into 93 mg (52%) of 619 after heating at 65° C. for 18 h.

Step 2. Deprotection of 61g to Give 62g

In accordance with the procedures of example 2, step 3, THP-ether 619 (93 mg, 0.19 mmol) was converted into 34 mg (44%) of alcohol 62g after a second equivalent portion of PPTs was added after 18 h and heating at 45° C. for an additional 24 h was conducted.

Step 3. Saponification of 62g to Give 63g

In accordance with the procedures of example 4, step 3, ester 62g (11 mg, 0.027 mmol) was converted into 7 mg (66%) of the title compound (63g) after purification by preparative thin layer chromatography eluting with 30% MeOH/CH$_2$Cl$_2$.

Example 32

5-(3-((1R,2S,3R,5R)-5-chloro-3-hydroxy-2-(pyridin-4-ylethynyl)cyclopentyl)propyl)thiophene-2-carboxylic acid (63h)

Step 1. Arylation of 60 to Give 61h

In accordance with the procedures of example 24, step 2, 60 (134 mg, 0.33 mmol) and 4-bromopyridine hydrochloride (111 mg, 0.57 mmol) were converted into 107 mg (67%) of 61h after heating at 65° C. for 18 h and using 3.5 equivalents of Cs$_2$CO$_3$.

Step 2. Deprotection of 61h to Give 62h

In accordance with the procedures of example 2, step 3, THP-ether 61h (107 mg, 0.22 mmol) was converted into 109 mg of impure crude alcohol 62h after a second equivalent portion of PPTs was added after 18 h and heating at 50° C. for an additional 24 h was conducted.

Step 3. Saponification of 62h to Give 63h

In accordance with the procedures of example 4, step 3, impure ester 62h (15 mg, ~0.037 mmol) was converted into 8 mg (~55%) of the title compound (63h) after purification by preparative thin layer chromatography eluting with 20% MeOH/CH$_2$Cl$_2$.

Scheme 11

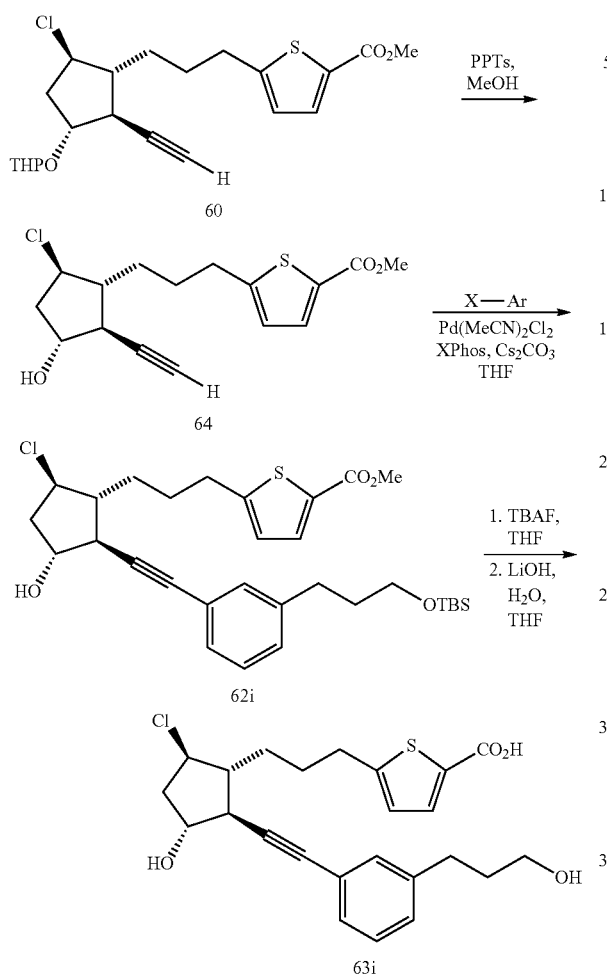

Preparation 10

(3-(3-bromophenyl)propoxy)(tert-butyl)dimethylsilane

Step 1. 3-(3-bromophenyl)propan-1-ol

A solution of 1-allyl-3-bromobenzene (998 mg, 5.1 mmol) in THF (2 mL+0.5 mL) was added to a solution of 9-BBN dimer (806 mg, 3.3 mol) in THF (6.6 mL). The mixture was stirred overnight at room temperature, then 3.0 M NaOH (2 mL) and 30% $H_2O_2$ (2 mL) were added while cooling the reaction mixture in an ice bath to control the exotherm. The mixture was stirred at room temperature for 4 h and then partitioned between brine (20 mL) and EtOAc (20 mL). The layers were separated and the aqueous phase was extracted with EtOAc (20 mL). The combined organic phase was dried ($Na_2SO_4$), filtered and concentrated in vacuo. Purification of the crude residue by chromatography on 80g silica gel (hexanes 60% EtOAc/hexanes, gradient) afforded 637 mg (58%) of 3-(3-bromophenyl)propan-1-ol.

Step 2. (3-(3-bromophenyl)propoxy)(tert-butyl)dimethylsilane t-Butyldimethylsilyl chloride (3.26 g, 21.7 mmol) was added to a solution of 3-(3-bromophenyl)propan-1-ol (3.15 g, 14.7 mmol), triethylamine (4.1 mL, 29.4 mmol) and DMAP (364 mg, 3.0 mmol) in $CH_2Cl_2$ (30 mL). After stirring at room temperature for 18 h, the reaction was quenched with saturated aqueous $NaHCO_3$ (100 mL) and the mixture was extracted with $CH_2Cl_2$ (50 mL). The organic phase was washed with brine (100 mL) and then was dried ($Na_2SO_4$), filtered and concentrated in vacuo. Purification of the crude residue by chromatography on 120g silica gel (10% EtOAc/hexanes→35% EtOAc/hexanes, gradient) afforded 4.36 g (90%) of the title compound.

Example 33

5-(3-((1R,2S,3R,5R)-5-chloro-3-hydroxy-2-((3-(3-hydroxypropyl)phenyl)ethynyl)cyclopentyl)propyl)thiophene-2-carboxylic acid (63i)

Step 1. Deprotection of 60 to Give 64

In accordance with the procedures of example 2, step 3, THP-ether 60 (121 mg, 0.29 mmol) was converted into 62 mg (65%) of alcohol 64 after purification on 40g silica gel (hexane→50% EtOAc/hexanes, gradient).

Step 2. Arylation of 64 to Give 62i

In accordance with the procedures of example 24, step 2, 64 (292 mg, 0.89 mmol) and (3-(3-bromophenyl)propoxy)(tert-butyl)dimethylsilane (preparation 10, 286 mg, 0.87 mmol) were converted into 321 mg (64%) of 62i after purification on 40g silica gel (hexane→45% EtOAc/hexanes, gradient).

Step 3. Deprotection and Saponification of 62i to Give 63i

TBAF (0.10 mL of a 1.0 M solution in THF, 0.10 mmol) was added to a solution of 62i (13 mg, 0.023 mmol) in THF (0.10 mL). After stirring 21 h at room temperature, the reaction was partitioned between saturated aqueous $NH_4Cl$ (10 mL) and EtOAc (20 mL). The layers were separated and the aqueous phase was extracted with EtOAc (20 mL). The combined organic phase was dried ($Na_2SO_4$), filtered and concentrated in vacuo. The crude material was then treated in accordance with the procedures of example 4, step 3, to afford 5 mg (49%) of the title compound (63i) after heating at 60° C. for 18 h and after purification by chromatography thin layer chromatography eluting with 7.5% MeOH/$CH_2Cl_2$.

Scheme 12

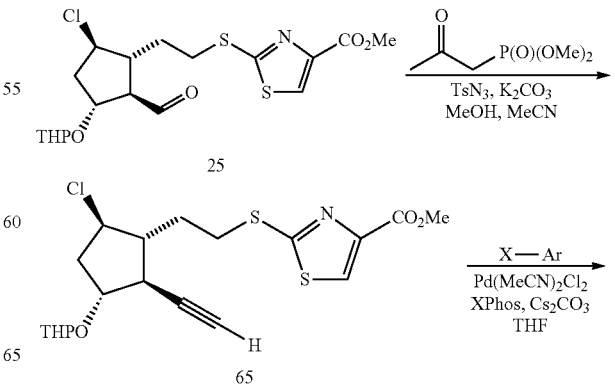

-continued

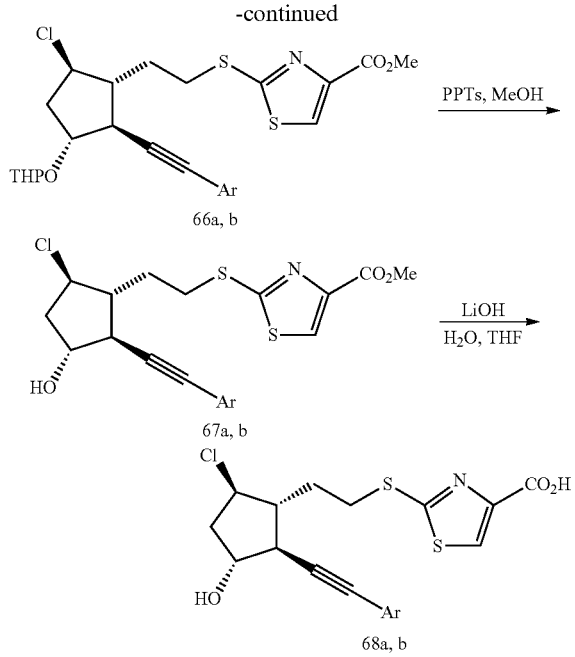

Example 34

2-(2-((1R,2S,3R,5R)-5-chloro-2-((3,5-dichlorophenyl)ethynyl)-3-hydroxycyclopentyl)ethylthio)thiazole-4-carboxylic acid (68a)

Step 1. Reaction of 25 to Give 65

In accordance with the procedures of example 24, step 1, crude aldehyde 25 (prepared in accordance with the procedure of examples 2 and 14, step 1, ~5.85 mmol) was converted to 600 mg (23%) of alkyne 65.

Step 2. Arylation of 65 to Give 66a

In accordance with the procedures of example 24, step 2, 65 (100 mg, 0.23 mmol) and 1-bromo-3,5-dichlorobenzene (102 mg, 0.45 mmol) were converted into 21 mg (16%) of 66a after heating at 60° C. for 18 h.

Step 3. Deprotection of 66a to Give 67a

In accordance with the procedures of example 2, step 3, THP-ether 66a (21 mg, 0.036 mmol) was converted into 4 mg (22%) of alcohol 67a.

Step 4. Saponification of 67a to Give 68a

In accordance with the procedures of example 4, step 3, ester 67a (3 mg, 0.059 mmol) was converted into 2 mg (71%) of the title compound (68a) after purification by preparative thin layer chromatography eluting with 20% MeOH/CH$_2$Cl$_2$.

Example 35

2-(2-((1R,2S,3R,5R)-5-chloro-3-hydroxy-2-(phenylethynyl)cyclopentyl)ethylthio)thiazole-4-carboxylic acid (68b)

Step 1. Arylation of 65 to Give 66b

In accordance with the procedures of example 24, step 2, 65 (100 mg, 0.23 mmol) and bromobenzene (47 µL, 0.45 mmol) were converted into 20 mg (17%) of 66b after heating at 60° C. for 18 h.

Step 2. Deprotection of 66b to Give 67b

In accordance with the procedures of example 2, step 3, THP-ether 66b (20 mg, 0.038 mmol) was converted into 11 mg (66%) of alcohol 67b Step 3. Saponification of 67b to Give 68b In accordance with the procedures of example 4, step 3, ester 67b (6 mg, 0.014 mmol) was converted into 4 mg (71%) of the title compound (68b) after purification by preparative thin layer chromatography eluting with 20% MeOH/CH$_2$Cl$_2$.

In Vitro Testing

U.S. patent application Ser. No. 11/553,143, filed on Oct. 26, 2006, incorporated by reference herein in its entirety, describes the methods used to obtain the in vitro data in the table below.

| Example # | Structure | EP2 data | | | EP4 data | | Other Receptors (EC50 in nM) | | | | |
|---|---|---|---|---|---|---|---|---|---|---|---|
| | | flipr EC50 | cAMP EC50 | Ki | flipr EC50 | Ki | hFP | hEP1 | hEP3A | hTP | tIP | hDP |
| 1 | | 37 | 0.2 | 2.2 | >10000 | 440 | NA | NA | >10000 | >10000 | NA | NA |

-continued
| Example # | Structure | EP2 data | | | EP4 data | | Other Receptors (EC50 in nM) | | | | | |
|---|---|---|---|---|---|---|---|---|---|---|---|---|
| | | flipr EC50 | cAMP EC50 | Ki | flipr EC50 | Ki | hFP | hEP1 | hEP3A | hTP | tIP | hDP |
| 2 | 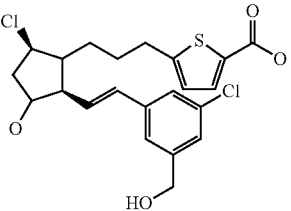 [SMILES: O=C(O)c1ccc(CCCC2[C@@H](/C=C/c3cc(Cl)cc(CO)c3)C(O)C[C@H]2Cl)s1] | 85 | 0.13 | 2 | >10000 | 135 | NA | NA | NA | NA | NA | >10000 |
| 3 | 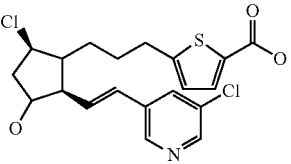 [SMILES: O=C(O)c1ccc(CCCC2[C@@H](/C=C/c3cncc(Cl)c3)C(O)C[C@H]2Cl)s1] | 101 | 1.3 | 10 | 15893 | 43989 | NA | NA | NA | NA | NA | NA |
| 4 | 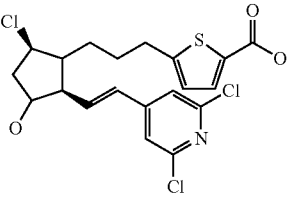 [SMILES: O=C(O)c1ccc(CCCC2[C@@H](/C=C/c3cc(Cl)nc(Cl)c3)C(O)C[C@H]2Cl)s1] | 44 | 0.09 | 2.3 | 15856 | 162 | NA | NA | NA | NA | NA | NA |
| 5 | 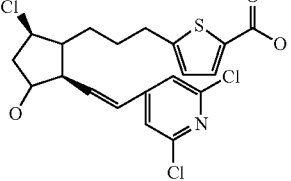 | 458 | 3 | 38 | 1923 | 1986 | NA | NA | NA | NA | NA | 2095 |
| 6 | 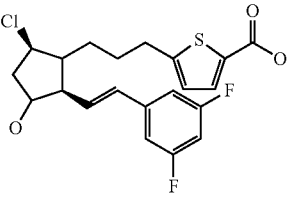 [SMILES: O=C(O)c1ccc(CCCC2[C@@H](/C=C/c3cc(F)cc(F)c3)C(O)C[C@H]2Cl)s1] | 22 | 0.3 | 7 | >10000 | 876 | NA | NA | NA | 85346 | NA | NA |
| 7 | 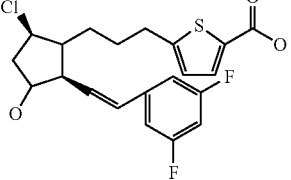 | 7135 | 207 | 425 | | 3219 | NA | NA | NA | 95 | NA | 6389 |
| 8 | 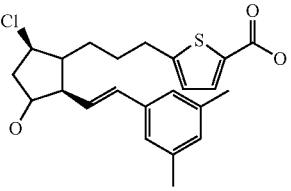 [SMILES: Cc1cc(C)cc(/C=C/[C@H]2C(O)C[C@@H](Cl)C2CCCc2ccc(C(=O)O)s2)c1] | 328 | 1.4 | 8 | 10016 | 86 | NA | NA | NA | NA | NA | NA |

| Example # | Structure | EP2 data flipr EC50 | EP2 data cAMP EC50 | EP2 data Ki | EP4 data flipr EC50 | EP4 data Ki | Other Receptors (EC50 in nM) hFP | hEP1 | hEP3A | hTP | tIP | hDP |
|---|---|---|---|---|---|---|---|---|---|---|---|---|
| 9 | 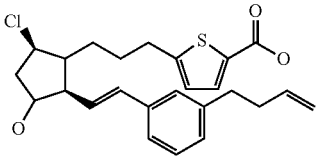 [SMILES: C=CCCc1cccc(/C=C/[C@H]2C(O)C[C@@H](Cl)C2CCCc2ccc(C(=O)O)s2)c1] | 72 | 0.03 | 0.7 | 17315 | 286 | NA | NA | 5783 | NA | NA | NA |
| 10 | 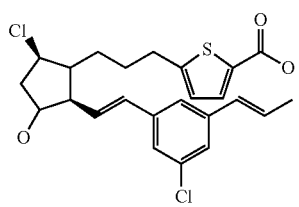 [SMILES: C/C=C/c1cc(Cl)cc(/C=C/[C@H]2C(O)C[C@@H](Cl)C2CCCc2ccc(C(=O)O)s2)c1] | 1543 | 0.1 | 1.4 | >10000 | 90 | NA | NA | NA | NA | NA | NA |
| 11 | 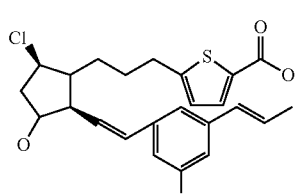 | 2164 | 12 | 24 | 6459 | 239 | NA | NA | NA | NA | NA | NA |
| 12 | 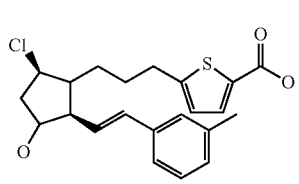 [SMILES: Cc1cccc(/C=C/[C@H]2C(O)C[C@@H](Cl)C2CCCc2ccc(C(=O)O)s2)c1] | 17 | 0.1 | 2 | 16858 | 144 | NA | NA | 9877 | 3783 | NA | 12295 |
| 13 | 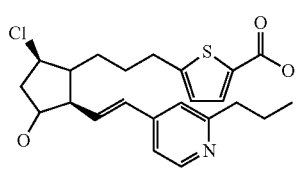 [SMILES: CCCc1cc(/C=C/[C@H]2C(O)C[C@@H](Cl)C2CCCc2ccc(C(=O)O)s2)ccn1] | >10000 | 0.4 | 2 | >10000 | 193 | NA | NA | NA | NA | NA | NA |
| 14 | 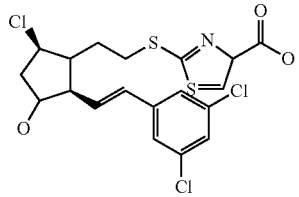 | 7 | 0.04 | 1.2 | 3462 | 616 | NA | NA | 3883 | NA | NA | NA |
| 15 | 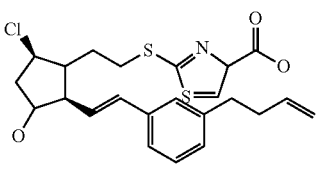 | 5 | 0.08 | 0.6 | 250 | 259 | NA | >10000 | 140 | NA | NA | >10000 |
| 16 | 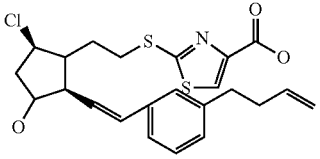 [SMILES: C=CCCc1cccc(C=C[C@H]2C(O)C[C@@H](Cl)C2CCSc2nc(C(=O)O)cs2)c1] | 11 | 2 | 33 | 5447 | 2043 | NA | >10000 | 262 | NA | NA | >10000 |

-continued

| Example # | Structure | EP2 data | | | EP4 data | | Other Receptors (EC50 in nM) | | | | | |
|---|---|---|---|---|---|---|---|---|---|---|---|---|
| | | flipr EC50 | cAMP EC50 | Ki | flipr EC50 | Ki | hFP | hEP1 | hEP3A | hTP | tIP | hDP |
| 17 | 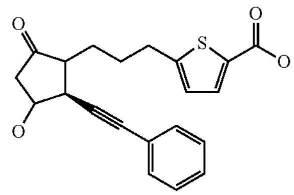 [SMILES: O=C(O)c1ccc(CCCC2C(=O)CC(O)[C@@H]2C#Cc2ccccc2)s1] | 9 | 0.05 | 5 | 33750 | 700 | NA | NA | 11041 | NA | NA | NA |
| 18 | 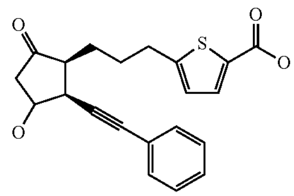 [SMILES: O=C(O)c1ccc(CCC[C@@H]2C(=O)CC(O)[C@@H]2C#Cc2ccccc2)s1] | 22 | 0.6 | 30 | 3222 | 1792 | NA | NA | NA | NA | NA | NA |
| 19 | 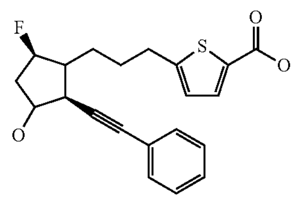 [SMILES: O=C(O)c1ccc(CCCC2[C@@H](C#Cc3ccccc3)C(O)C[C@H]2F)s1] | 349 | 0.25 | 4 | 26604 | 1022 | NA | NA | >10000 | NA | NA | NA |
| 20 | 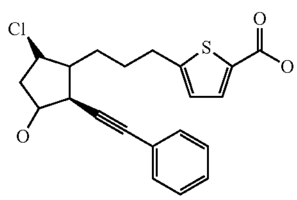 | 221 | 0.03 | 0.5 | 630 | 114 | NA | >10000 | 4027 | NA | NA | >10000 |
| 22 | 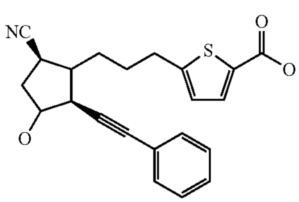 [SMILES: N#C[C@@H]1CC(O)[C@H](C#Cc2ccccc2)C1CCCc1ccc(C(=O)O)s1] | 235 | 0.18 | 13 | 21225 | 567 | NA | NA | >10000 | NA | NA | NA |
| 23 | 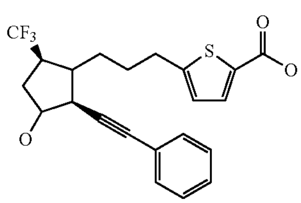 [SMILES: O=C(O)c1ccc(CCCC2[C@@H](C#Cc3ccccc3)C(O)C[C@H]2C(F)(F)F)s1] | 79 | 3 | 30 | | | NA | NA | 7996 | NA | NA | NA |
| 24 | 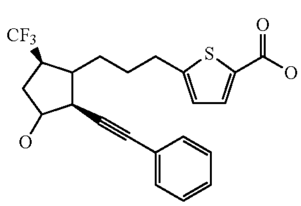 [SMILES: O=C(O)c1ccc(CCCC2[C@@H](C#Cc3ccccc3)C(O)C[C@H]2C(F)(F)F)s1] | 107 | 4 | 41 | | | NA | NA | NA | NA | NA | NA |

-continued
| Example # | Structure | EP2 data | | | EP4 data | | Other Receptors (EC50 in nM) | | | | | |
|---|---|---|---|---|---|---|---|---|---|---|---|---|
| | | flipr EC50 | cAMP EC50 | Ki | flipr EC50 | Ki | hFP | hEP1 | hEP3A | hTP | tIP | hDP |
| 25 | 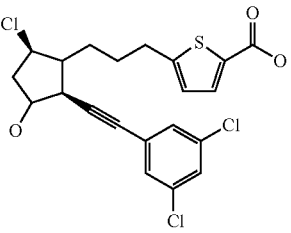 [SMILES: O=C(O)c1ccc(CCCC2[C@@H](C#Cc3cc(Cl)cc(Cl)c3)C(O)C[C@H]2Cl)s1] | 135 | 0.00 | <0.06 | 1806 | 466 | NA | NA | NA | NA | NA | NA |
| 26 | 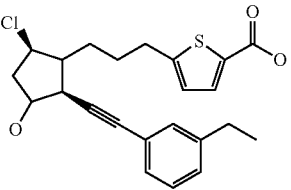 [SMILES: CCc1cccc(C#C[C@H]2C(O)C[C@@H](Cl)C2CCCc2ccc(C(=O)O)s2)c1] | 56 | 0.08 | 0.3 | 616 | 316 | NA | NA | NA | NA | NA | NA |
| 27 | 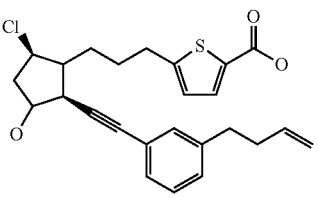 [SMILES: C=CCCc1cccc(C#C[C@H]2C(O)C[C@@H](Cl)C2CCCc2ccc(C(=O)O)s2)c1] | 19 | 0.03 | 1 | 10985 | 436 | NA | NA | NA | NA | NA | NA |
| 28 | 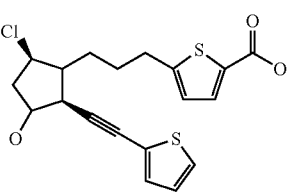 [SMILES: O=C(O)c1ccc(CCCC2[C@@H](C#Cc3cccs3)C(O)C[C@H]2Cl)s1] | | 0.6 | 10 | 5679 | 825 | NA | NA | 8521 | NA | NA | 18345 |
| 29 | 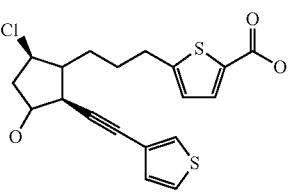 [SMILES: O=C(O)c1ccc(CCCC2[C@@H](C#Cc3ccsc3)C(O)C[C@H]2Cl)s1] | | 3.3 | 64 | 5910 | 1875 | NA | NA | NA | NA | NA | NA |
| 30 | 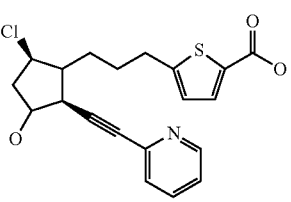 [SMILES: O=C(O)c1ccc(CCCC2[C@@H](C#Cc3ccccn3)C(O)C[C@H]2Cl)s1] | 3 | 0.2 | 11 | >10000 | 2141 | NA | NA | NA | NA | NA | NA |
| 31 | 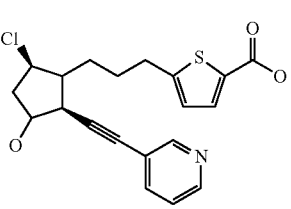 [SMILES: O=C(O)c1ccc(CCCC2[C@@H](C#Cc3cccnc3)C(O)C[C@H]2Cl)s1] | 2 | 0.3 | 4 | 4195 | 1446 | NA | NA | NA | NA | NA | NA |

| Example # | Structure | EP2 data flipr EC50 | cAMP EC50 | Ki | EP4 data flipr EC50 | Ki | Other Receptors (EC50 in nM) hFP | hEP1 | hEP3A | hTP | tIP | hDP |
|---|---|---|---|---|---|---|---|---|---|---|---|---|
| 32 | 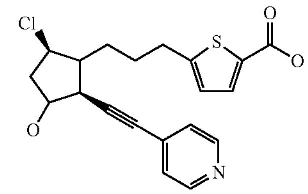 [SMILES: O=C(O)c1ccc(CCCC2[C@@H](C#Cc3ccncc3)C(O)C[C@H]2Cl)s1] | 306 | 7 | 79 | >10000 | 8669 | NA | NA | NA | NA | NA | NA |
| 33 | 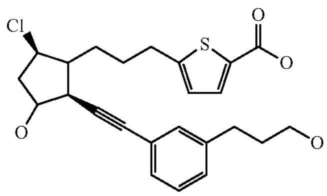 [SMILES: O=C(O)c1ccc(CCCC2[C@@H](C#Cc3cccc(CCCO)c3)C(O)C[C@H]2Cl)s1] | | 0.22 | 2 | 8991 | 1524 | NA | NA | NA | NA | NA | NA |
| 34 | 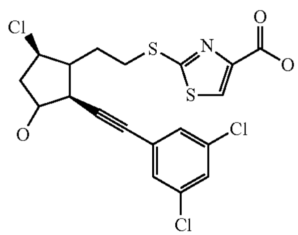 [SMILES: O=C(O)c1csc(SCCC2[C@@H](C#Cc3cc(Cl)cc(Cl)c3)C(O)C[C@H]2Cl)n1] | 5.16 | 1.5 | | 3.3 | 60 | NA | NA | 2876 | NA | NA | 14810 |
| 35 | 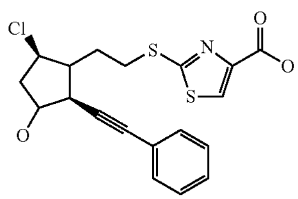 [SMILES: O=C(O)c1csc(SCCC2[C@@H](C#Cc3ccccc3)C(O)C[C@H]2Cl)n1] | 0.6 | 5 | | 10 | 463 | NA | NA | 1900 | NA | NA | 1031 |

What is claimed is:

1. A compound having a formula

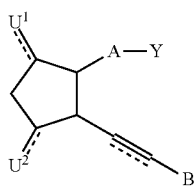

or a pharmaceutically acceptable salt thereof, wherein a dashed line represents the presence or absence of a bond;

Y is $COR^4$ or $CONR^5R^6$, wherein $R^4$, $R^5$, and $R^6$ are independently H or $C_2$-$C_6$ alkyl; or Y is hydroxymethyl or an ether thereof; or Y is a tetrazolyl functional group;

A is cis —$CH_2CH$=$CH$—$(CH_2)_3$— or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —$CH$=$CH$— or —$C$≡$C$—;

$U^1$ and $U^2$ are independently selected from —H, =O, —OH, —F, —Cl, and —CN; and B is aryl or heteroaryl, provided that if $U^1$ is =O, $U^2$ is not —OH or —H.

2. A compound having a formula

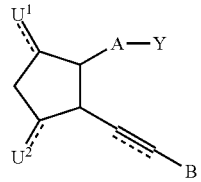

or a pharmaceutically acceptable salt thereof, wherein a dashed line represents the presence or absence of a bond;

Y is $CO_2R^4$ or $CONR^5R^6$, wherein $R^4$, $R^5$, and $R^6$ are independently H or $C_2$-$C_6$ alkyl; or Y is hydroxymethyl or an ether thereof; or Y is a tetrazolyl functional group;

A is cis —CH$_2$CH═CH—(CH$_2$)$_3$— or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$— may be replaced by —CH═CH— or —C≡C—;
U$^1$ is —H, —OH, —F, —Cl, or —CN;
U$^2$ is —H, ═O, —OH, —F, —Cl, or —CN; and
B is aryl or heteroaryl.

3. A compound having a formula

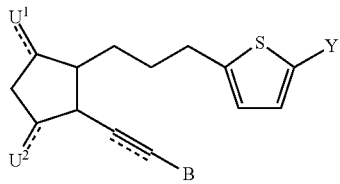

or a pharmaceutically acceptable salt thereof, wherein a dashed line represents the presence or absence of a bond;
Y is CO$_2$R$^4$ or CONR$^5$R$^6$, wherein R$^4$, R$^5$, and R$^6$ are independently H or C$_2$-C$_6$ alkyl; or Y is hydroxymethyl or an ether thereof; or Y is a tetrazolyl functional group;
U$^1$ and U$^2$ are independently selected from —H, ═O, —OH, —F, —Cl, and —CN; and
B is aryl or heteroaryl.

4. The compound according to claim 1, wherein B is substituted phenyl or pyridinyl.

5. The compound according to claim 1, wherein U$^1$ is ═O.

6. The compound according to claim 1, wherein U$^1$ is —H.

7. The compound according to claim 1, wherein U$^1$ is —OH.

8. The compound according to claim 1, wherein U$^1$ is —F.

9. The compound according to claim 1, wherein U$^1$ is —Cl.

10. The compound according to claim 1, wherein U$^1$ is —CN.

11. The compound according to claim 5, wherein U$^2$ is ═O.

12. The compound according to claim 6, wherein U$^2$ is —H.

13. The compound according to claim 6, wherein U$^2$ is —OH.

14. The compound according to claim 5, wherein U$^2$ is —F.

15. The compound according to claim 5, wherein U$^2$ is —Cl.

16. The compound according to claim 5, wherein U$^2$ is —CN.

17. The compound of claim 2 having a formula

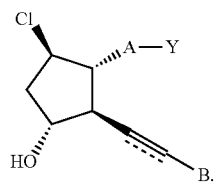

18. The compound according to claim 4 wherein B is substituted with substituents selected from F, Cl, C$_{1-3}$ alkyl, and hydroxyalkyl having from 1 to 3 carbon atoms.

19. The compound of claim 17, wherein B is selected from

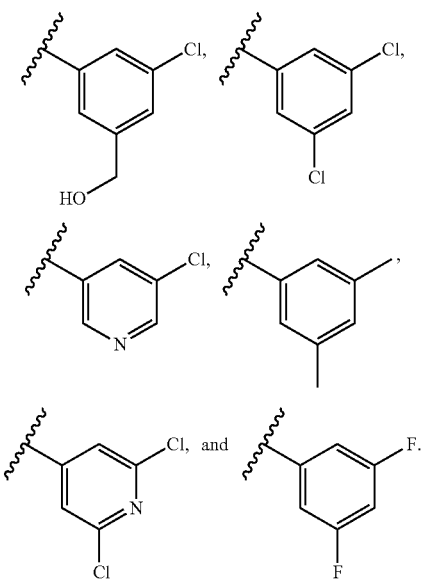

20. The compound of claim 19, said compound selected from:

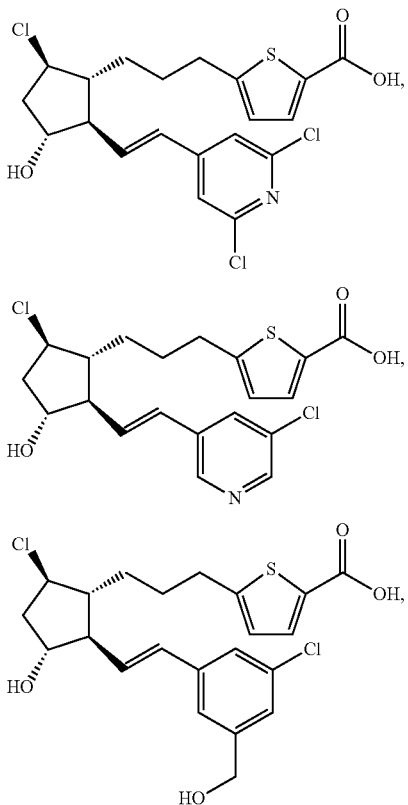

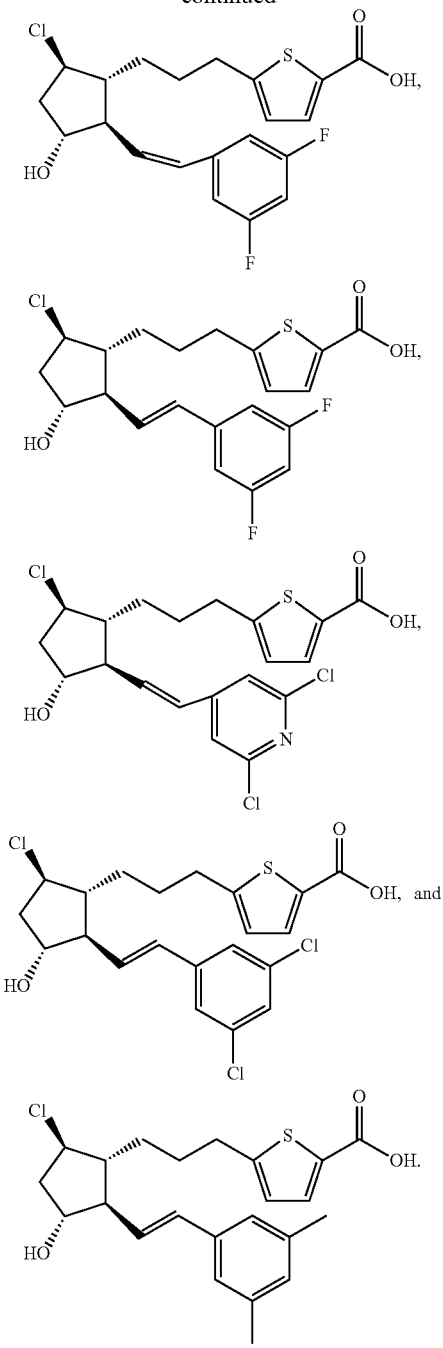

21. A compound wherein the compound is selected from the group consisting of:
- 5-(3-((1R,2R,3R,5R)-5-chloro-2-(3,5-dichlorostyryl)-3-hydroxycyclopentyl)prop-1-enyl)thiophene-2-carboxylic acid;
- 5-(3-((1R,2R,3R,5R)-5-chloro-2-(3-chloro-5-(hydroxymethyl)styryl)-3-hydroxycyclopentyl)propyl)-thiophene-2-carboxylic acid;
- 5-(3-((1R,2R,3R,5R)-5-chloro-2-((E)-2-(5-chloropyridin-3-yl)vinyl)-3-hydroxycyclopentyl)propyl)-thiophene-2-carboxylic acid;
- 5-(3-((1R,2R,3R,5R)-5-chloro-2-((E)-2-(2,6-dichloropyridin-4-yl)vinyl)-3-hydroxycyclopentyl)propyl)-thiophene-2-carboxylic acid;
- 5-(3-((1R,2R,3R,5R)-5-chloro-2-((Z)-2-(2,6-dichloropyridin-4-yl)vinyl)-3-hydroxycyclopentyl)propyl)-thiophene-2-carboxylic acid;
- 5-(3-((1R,2R,3R,5R)-5-chloro-2-((E)-3,5-difluorostyryl)-3-hydroxycyclopentyl)propyl)thiophene-2-carboxylic acid;
- 5-(3-((1R,2R,3R,5R)-5-chloro-2-((Z)-3,5-difluorostyryl)-3-hydroxycyclopentyl)propyl)thiophene-2-carboxylic acid;
- 5-(3-((1R,2R,3R,5R)-5-chloro-2-(3,5-dimethylstyryl)-3-hydroxycyclopentyl)propyl)thiophene-2-carboxylic acid;
- 5-(3-((1R,2R,3R,5R)-2-(3-(but-3-enyl)styryl)-5-chloro-3-hydroxycyclopentyl)propyl)thiophene-2-carboxylic acid;
- 5-(3-((1R,2R,3R,5R)-5-chloro-2-((E)-3-chloro-5-((E)-prop-1-enyl)styryl)-3-hydroxycyclopentyl)propyl)thiophene-2-carboxylic acid;
- 5-(3-((1R,2R,3R,5R)-5-chloro-2-((Z)-3-chloro-5-((E)-prop-1-enyl)styryl)-3-hydroxycyclopentyl)propyl)thiophene-2-carboxylic acid;
- 5-(3-((1R,2R,3R,5R)-5-chloro-3-hydroxy-2-(3-methylstyryl)cyclopentyl)propyl)thiophene-2-carboxylic acid;
- 5-(3-((1R,2R,3R,5R)-5-chloro-3-hydroxy-2-((E)-2-(2-propylpyridin-4-yl)vinyl)cyclopentyl)propyl)thiophene-2-carboxylic acid;
- 2-(2-((1R,2R,3R,5R)-5-chloro-2-(3,5-dichlorostyryl)-3-hydroxycyclopentyl)ethylthio)thiazole-4-carboxylic acid;
- 2-(2-((1R,2R,3R,5R)-2-((E)-3-(but-3-enyl)-5-chlorostyryl)-5-chloro-3-hydroxycyclopentyl)ethylthio)thiazole-4-carboxylic acid;
- 2-(2-((1R,2R,3R,5R)-2-((Z)-3-(but-3-enyl)-5-chlorostyryl)-5-chloro-3-hydroxycyclopentyl)ethylthio)thiazole-4-carboxylic acid;
- 5-(3-((1R,2S,3R)-3-hydroxy-5-oxo-2-(phenylethynyl)cyclopentyl)propyl)thiophene-2-carboxylic acid;
- 5-(3-((1S,2S,3R)-3-hydroxy-5-oxo-2-(phenylethynyl)cyclopentyl)propyl)thiophene-2-carboxylic acid;
- 5-(3-((1R,2S,3R,5R)-5-fluoro-3-hydroxy-2-(phenylethynyl)cyclopentyl)propyl)thiophene-2-carboxylic acid;
- 5-(3-((1R,2S,3R,5R)-5-chloro-3-hydroxy-2-(phenylethynyl)cyclopentyl)propyl)thiophene-2-carboxylic acid;
- Isopropyl 5-(3-((1R,2S,3R,5R)-5-chloro-3-hydroxy-2-(phenylethynyl)cyclopentyl)propyl)thiophene-2-carboxylate;
- 5-(3-((1S,2S,3R,5R)-5-cyano-3-hydroxy-2-(phenylethynyl)cyclopentyl)propyl)thiophene-2-carboxylic acid;
- 5-(3-((1R,2S,3R)-3-hydroxy-2-(phenylethynyl)-5-(trifluoromethyl)cyclopentyl)propyl)thiophene-2-carboxylic acid (faster eluting HPLC diastereomer);
- 5-(3-((1R,2S,3R)-3-hydroxy-2-(phenylethynyl)-5-(trifluoromethyl)cyclopentyl)propyl)thiophene-2-carboxylic acid (slower eluting HPLC diastereomer);
- 5-(3-((1R,2S,3R,5R)-5-chloro-2-((3,5-dichlorophenyl)ethynyl)-3-hydroxycyclopentyl)propyl)thiophene-2-carboxylic acid;
- 5-(3-((1R,2S,3R,5R)-5-chloro-2-(3-ethylphenyl)ethynyl)-3-hydroxycyclopentyl)propyl)thiophene-2-carboxylic acid;
- 5-(3-((1R,2S,3R,5R)-2-((3-(but-3-enyl)phenyl)ethynyl)-5-chloro-3-hydroxycyclopentyl)propyl)thiophene-2-carboxylic acid;
- 5-(3-((1R,2S,3R,5R)-5-chloro-3-hydroxy-2-(thiophen-2-ylethynyl)cyclopentyl)propyl)thiophene-2-carboxylic acid;

5-(3-((1R,2S,3R,5R)-5-chloro-3-hydroxy-2-(thiophen-3-ylethynyl)cyclopentyl)propyl)thiophene-2-carboxylic acid;
5-(3-((1R,2S,3R,5R)-5-chloro-3-hydroxy-2-(pyridin-2-ylethynyl)cyclopentyl)propyl)thiophene-2-carboxylic acid;
5-(3-((1R,2S,3R,5R)-5-chloro-3-hydroxy-2-(pyridin-3-ylethynyl)cyclopentyl)propyl)thiophene-2-carboxylic acid;
5-(3-((1R,2S,3R,5R)-5-chloro-3-hydroxy-2-(pyridin-4-ylethynyl)cyclopentyl)propyl)thiophene-2-carboxylic acid;
5-(3-((1R,2S,3R,5R)-5-chloro-3-hydroxy-2-((3-(3-hydroxypropyl)phenyl)ethynyl)cyclopentyl)propyl)thiophene-2-carboxylic acid;
2-(2-((1R,2S,3R,5R)-5-chloro-2-((3,5-dichlorophenyl)ethynyl)-3-hydroxycyclopentyl)ethylthio)thiazole-4-carboxylic acid; and,
2-(2-((1R,2S,3R,5R)-5-chloro-3-hydroxy-2-(phenylethynyl)cyclopentyl)ethylthio)thiazole-4-carboxylic acid;
or a pharmaceutically acceptable salt thereof.

\* \* \* \* \*